United States Patent
Crosby et al.

(10) Patent No.: US 12,263,257 B2
(45) Date of Patent: Apr. 1, 2025

(54) FAR UV-C APPARATUS AND CONFIRMATION OF USE

(71) Applicant: Crosby Innovations, LLC, Detroit, MI (US)

(72) Inventors: Douglas A. Crosby, Port Huron, MI (US); Fred Maxik, Orlando, FL (US)

(73) Assignee: Crosby Innovations, LLC, Detroit, MI (US)

( * ) Notice: Subject to any disclaimer, the term of this patent is extended or adjusted under 35 U.S.C. 154(b) by 187 days.

(21) Appl. No.: 17/744,482

(22) Filed: May 13, 2022

(65) Prior Publication Data
US 2022/0273833 A1    Sep. 1, 2022

Related U.S. Application Data

(60) Continuation-in-part of application No. 17/357,893, filed on Jun. 24, 2021, which is a continuation-in-part (Continued)

(51) Int. Cl.
*A61L 2/00*        (2006.01)

(52) U.S. Cl.
CPC ......... *A61L 2/0047* (2013.01); *A61L 2202/11* (2013.01); *A61L 2202/14* (2013.01)

(58) Field of Classification Search
CPC ...... A61L 2/10; A61L 2/0047; A61L 2202/11; A61L 2202/14
See application file for complete search history.

(56) References Cited

U.S. PATENT DOCUMENTS

| | | | |
|---|---|---|---|
| 2015/0209457 A1* | 7/2015 | Bonutti | C02F 1/325 250/435 |
| 2018/0169279 A1* | 6/2018 | Randers-Pehrson | A61N 5/0624 |

(Continued)

FOREIGN PATENT DOCUMENTS

| | | | | |
|---|---|---|---|---|
| CN | 101366956 A | * | 2/2009 | |
| JP | 2010024572 A | * | 2/2010 | |
| WO | WO-2016042879 A1 | * | 3/2016 | A61L 2/0047 |

OTHER PUBLICATIONS

Translation for JP-2010024572-A (Year: 2010).*
Translation of CN-101366956-A (Year: 2009).*
Translation for WO-2016042879-A1 (Year: 2016).*

*Primary Examiner* — Sean E Conley
(74) *Attorney, Agent, or Firm* — Foster Swift Collins & Smith PC; Mikhail Murshak

(57) ABSTRACT

A UV-C sanitizing apparatus includes a main body defining an opening configured for receiving an item to be exposed to UV-C light emission. A plurality of UV-C light emitting diodes (LEDs) are positioned within the main body and are configured to emit UV-C light to form a field for treatment. The LEDs are positioned on lower and upper internal surfaces of the main body. The plurality of LEDs are configured to emit light at a wavelength between 205 and 210 nm. The UV-C light is configured to kill, destroy, or reduce growth of microorganisms and germs without damaging human tissue. The UV-C light can be configured to disinfect a surface of human hands or gloves or ocular tissue. The main body can include a partition configured to form separate chambers and each chamber includes a plurality of LEDs positioned on the lower and upper surfaces of the main body.

20 Claims, 20 Drawing Sheets

Related U.S. Application Data of application No. 17/194,268, filed on Mar. 7, 2021, now Pat. No. 11,607,469, which is a division of application No. 16/853,081, filed on Apr. 20, 2020, now Pat. No. 10,940,220, which is a continuation-in-part of application No. 15/975,262, filed on May 9, 2018, now Pat. No. 10,849,995.

(60) Provisional application No. 63/043,852, filed on Jun. 25, 2020, provisional application No. 63/000,186, filed on Mar. 26, 2020, provisional application No. 62/503,912, filed on May 9, 2017.

(56) References Cited

U.S. PATENT DOCUMENTS

| | | | |
|---|---|---|---|
| 2022/0062454 A1* | 3/2022 | Flaherty | A61L 2/0047 |
| 2022/0080060 A1* | 3/2022 | Jarvis | A61L 2/0076 |

\* cited by examiner

FAR UV-C APPARATUS AND CONFIRMATION OF USE

CROSS REFERENCE TO RELATED APPLICATION

This application is a continuation-in-part of U.S. patent application Ser. No. 17/357,893 filed Jun. 24, 2021 and titled Handheld UV-C Sanitizing Apparatus and Method which claims priority to U.S. Provisional Application No. 63/043,852 filed Jun. 25, 2020. Application Ser. No. 17/357,893 is a continuation-in-part of U.S. patent application Ser. No. 17/194,268 filed Mar. 7, 2021 which is a Divisional of U.S. application Ser. No. 16/853,081 filed Apr. 20, 2020, which claims priority to U.S. Provisional Application No. 63/000,186 filed Mar. 26, 2020 and U.S. application Ser. No. 16/853,081 is a continuation-in-part of U.S. patent application Ser. No. 15/975,262 filed on May 9, 2018, which claimed priority to U.S. Provisional Application No. 62/503,912 filed May 9, 2017. The present application claims priority to these applications which are hereby incorporated herein by reference in their entirety.

FIELD

The present disclosure relates generally to an apparatus, system, and method for sanitizing skin, tissue, or surfaces using UV-C light.

BACKGROUND

The statements in this section merely provide background information related to the present disclosure and may not constitute prior art.

There are various methods and devices that are capable of being utilized to remove germs, bacteria and/or other microorganisms. For example, it is known to use liquids, such as alcohols, acids and bases, to clean hands.

It is also known to use radiation, such as light, to clean objects by using the light to destroy microorganisms on the surface of the objects. For example, ultraviolet ("UV") light with a wavelength between approximately 100 to 290 nanometers (also referred to as "UV-C light") can be used as a germicide to destroy the DNA in microorganisms and thereby destroy the microorganisms. However, many of the devices that use UV-C light are large and bulky, making such devices difficult to move around and use with the ease of other bactericidal devices, like the liquid bactericidal discussed above. Moreover, some of the smaller UV-C light bactericidal devices are portable but may require a wired connection to an electrical outlet or are too large to carry around inconspicuously. There is a need for improved devices and methods for increased germicides and better hygiene without the need for liquids.

SUMMARY

The present disclosure provides for A UV-C sanitizing apparatus including: (a) a main body defining an opening configured for receiving an item to be exposed to UV-C light emission; (b) a plurality of UV-C light emitting diodes (LEDs) configured to emit UV-C light to form a field for treatment, the LEDS positioned on lower and upper internal surfaces of the main body; and (c) a circuit board coupled to the LEDS and a power source operable to deliver power to the LED unit. The plurality of LEDs are configured to emit light at a wavelength between 205 and 210 nm. The UV-C light is configured to kill, destroy, or reduce growth of microorganisms and germs without damaging human tissue.

In an example, the apparatus further includes an on/off button positioned along an outside surface of the main body and coupled to the power source. The button is configured for causing the LEDs to activate and deactivate. The power source can be a battery selected from the group consisting of a disposable battery and a rechargeable battery. The UV-C is configured to disinfect a surface of human hands or gloves. In another example, the UV light is sufficient to disinfect a surface of ocular tissue.

The present disclosure can include one or more visible colored or fluorescent lights configured to activate when the apparatus turns on as an indication that the apparatus is emitting UV-C light. The main body can include a partition configured to form separate chambers and each chamber includes a plurality of LEDs positioned on the lower and upper surfaces of the main body. The partition can extend fully or partially from the lower or upper surface of the main body configured to reduce or prevent waste emissions from escaping during use. The LEDS on the lower and upper surfaces of the main body are configured to sanitize from top and bottom sides of an item inserted through the opening simultaneously. The LEDS can be configured to radiate light at a minimum of 240 degrees from a cylindrical or tile encapsulant. The radiated light can be configured to be manipulated to create a field by which one or more items can be treated.

In yet another example, the UV-C sanitizing apparatus further comprises a sensor and a controller having a microprocessor configured to adjust dosing based on item size and time of exposure. The apparatus can further include a tracking module configured for tracking of users by compiling report data including number of uses and identification of users by biometric identification. The apparatus can include a filtering module configured for filtering output of the UV-C light at wavelengths above 222 nm or above 230 nm.

In still a further example, The UV-C sanitizing apparatus further includes a user identification system having a wireless communication module configured for automatic authentication and confirmation through a confirmation process. The user identification and authentication includes wireless communication protocols and modules selected from the group consisting of facial recognition, biometric identification, near field communications, and combinations thereof. The identification and authentication of a user can help determine dosing of time and exposure intensity of UV-C light. The dosing determination is configured to analyze biometric, pathogen, and dosing data to determine a daily exposure threshold such that daily exposure will not exceed regulatory limits.

The present disclosure provides for a handheld UV-C sanitizing apparatus including: (a) an enclosure defining an opening for light exposure; (b) a plurality of light emitting diodes (LEDs) mounted within the enclosure and configured to emit UV-C light out from the opening; (c) a circuit board positioned within the enclosure, wherein each LED is coupled to the circuit board and each LED is removable and replaceable independently; and (d) a power source coupled to the circuit board. The power source is configured to deliver power to each LED. The UV-C light emitted from the LEDs is at a wavelength suitable to kill, destroy, or reduce growth of microorganisms and germs in a preset exposure area directly below the UV-C light and safe for human skin exposure. The arrangement of the LEDs spaced apart from each other is configured to emit UV-C light into a field of exposure sufficient to cover the preset exposure area. The plurality of LEDs are configured to emit light at a wavelength between 205 and 210 nm.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings in which:

FIG. 20A-20B show photographs of example prototypes of a device having an equator light indicia strip to indicate on/off of the device and being held by a user with the user's hand in with the LED lights on;

Figure 1:
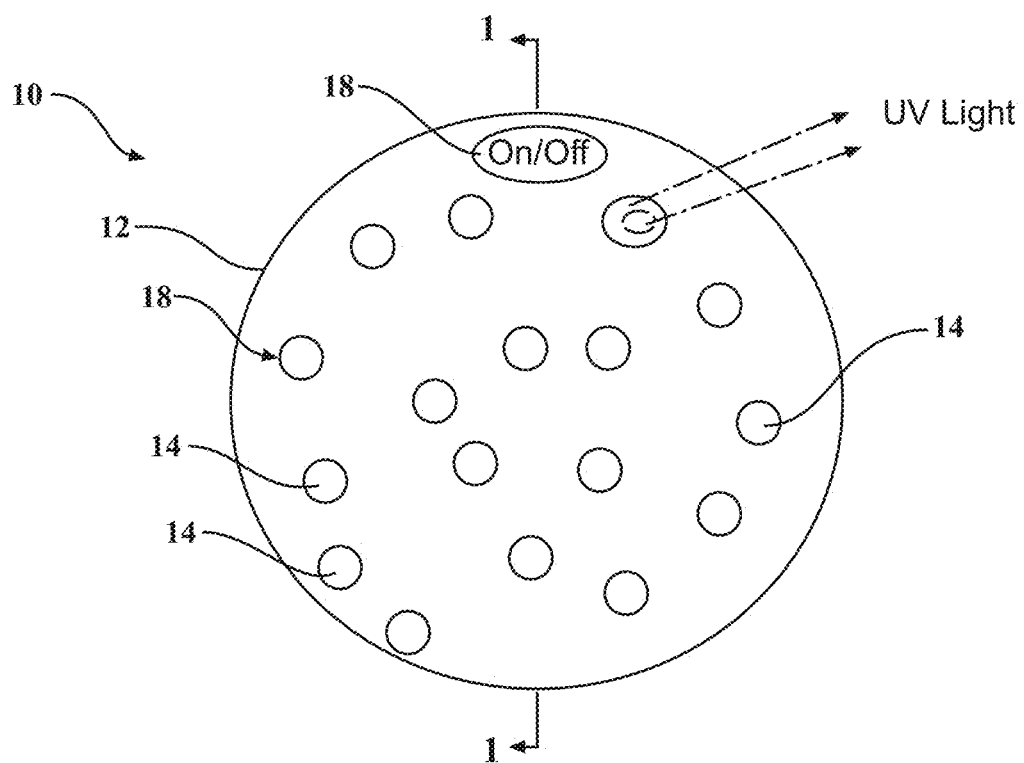
FIG. 1 illustrates a schematic of a device of the present disclosure with UV light emitting therefrom.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The present disclosure provides for an improved handheld sanitization and/or sterilization device capable of improved sanitizing and/or sterilizing an area proximate the device, such as skin, tissue or hands of a user. Ultraviolet (UV) light, specifically UV-C light, is an effective sterilization agent. The UV light breaks down living organisms to render them harmless. The device according to the present disclosure includes a plurality of UV emitting lights positioned within a housing. The UV light emitted from the device is operable to reduce, and improve the destroying of germs, bacteria, and/or viruses. The UV light referred to in this disclosure is short-wavelength ultraviolet "UV-C", which functions as a germicide and is less harmful than other wavelengths of UV light such as UV-A or UV-B. Accordingly, reference to "UV light" should be considered UV-C light for purposes of this disclosure.

Figure 2:
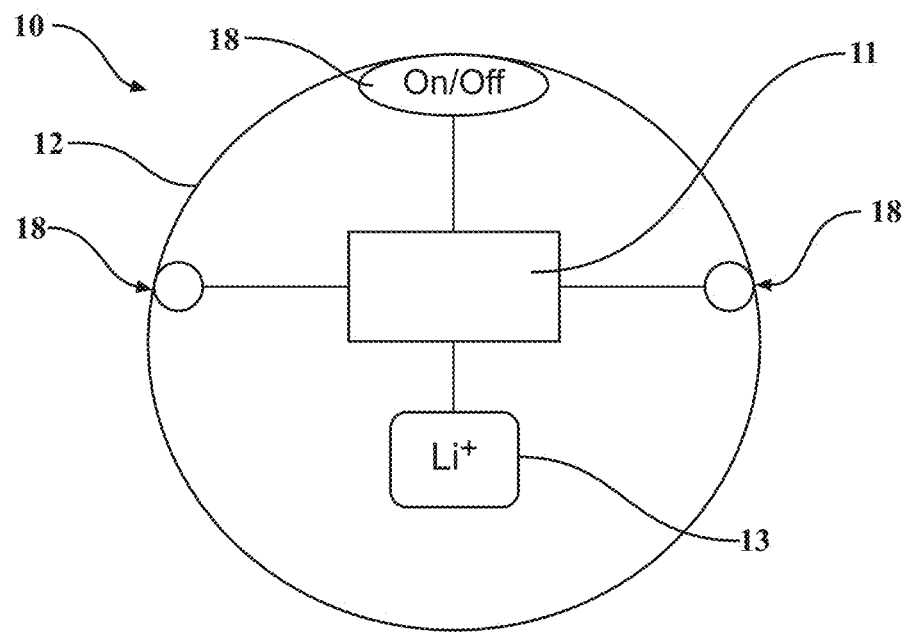
FIG. 2 is a cross section view of the device of FIG. 1 across line 1-1.
Figure 3:
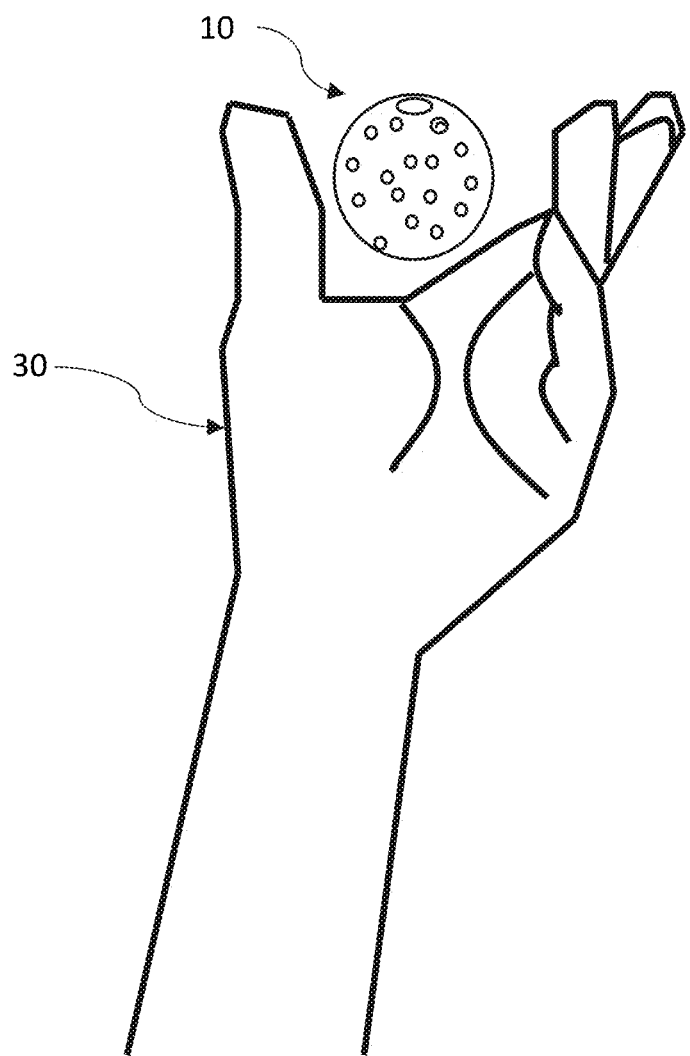
FIG. 3 illustrates the device of FIG. 1 in use being held by a hand of a user.

With reference now to the drawings, and particularly, FIGS. 1 to 3 illustrate an example embodiment of a handheld sanitization device 10 according to the present disclosure. In this example, device 10 includes a housing 12 defining a plurality of recessed openings 14 spaced apart and dispersed around the housing 12. Housing 12 can define any geometry, however, as shown in the drawings, housing 12 defines a spherical construction forming a "ball" with the recesses 14 spaced around an outer surface of housing 12. The housing 12 can be formed of any material suitable to contain additional components to be describe in further detail below. In an example, the housing 12 defines a surface fabricated from a polymer material having one or more colors as desired. For example, the surface of the housing 12 can be black or chrome. In another form, the surface can be any color. This can allow for the fabrication of a device 10 to capture a certain marketing theme or holiday, such as green for spring or orange for Halloween, for example.

In one form of the present disclosure, the handheld sanitization/sterilization device 10 is sized and shaped to fit easily within a user's hand. FIG. 3 illustrates a user's hand 40 holding an example device 10. The handheld device 10 allows for convenient transport in a user's pocket, purse, vehicle, or otherwise. Device 10 can be sized and shaped to define a diameter of about 1 to 3 inches, preferable about 2 inches.

Positioned within each recess 14 is at least one light emitting diode (LED) 16 operable to emit UV light through recess 14 when activated or turned "on" by an on/off switch/button 18. Recesses 14 can be generally rounded and define a diameter sufficient to allow for each LED 16 to have a diameter of about 3 mm to 5 mm. In an example, recess 14 should be formed to receive each LED 16 such that the surface of housing 12 is flush and thus the LED's 16 do not extend outward from the outer surface of housing 12.

The LEDs 16 are dispersed around housing 12 to allow for omnidirectional UV light emission. For example, this allows for UV light to be emitted in all directions and thus holding device 10 within a hand is sufficient to sanitize and/or sterilize most or possibly all surfaces of a user's hand.

On/off switch 18 is provided to allow activation of the plurality of LEDs 16 and thus device 10. Each LED 16 is adapted to emit UV light sufficient to sanitize or sterilize a surface within its proximity. The range for sterilization depends on the emission power of each LED 16. FIG. 2 illustrates an example cross section schematic view across line 1-1 to show internal components of device 10. In this example, each LED 16 is coupled to a circuit board 11 which is powered by a power source 13 such as a battery. In this example, a Lithium (Li+) ion battery or equivalent is used, however, disposable and/or rechargeable batteries are within the scope of this disclosure. The switch 18 is coupled to the circuit board 11 to send a signal to activate the LEDs 16. In this example, each LED 16 can be adapted to receive a current of about 20 mA and a power consumption of about 70 mW while delivering UV light having a wavelength in the range of between about 100 nm and 290 nm, 200 and 250 nm, 220 and 230 nm and/or between 254 nm and 265 nm.

In one form of the present disclosure, housing 12 can be formed to pivot open into two sections to allow for access to internal components. This allows for replacing and changing of those components such as LEDs 16 or battery 11. In yet another example, different colored LED lights are provided within housing 12 to create an alternative desired look and impression when activated. The UV light emitted from device 10 is UV-C light. It is contemplated that any fastening or connection system, such as a threaded connection or a clip in connection, to allow opening and closing of housing 12 is within the scope of the present disclosure (See FIGS. 7-9).

The present disclosure provides for a method of sterilizing/sanitizing hands of a user by providing a device 10 having a plurality of UV emitting LEDs 16 and activing the LEDs 16 to emit the UV light omnidirectional out from a housing 12 of device 10 to expose a user's hand to the UV light. In use, for example, a user may turn device 10 on by pushing on/off button 18 and thus activating the LEDs 16 to emit UV light and expose one or more hands 40 to the UV light by holding device 10 in their hand. Holding the device 10 for several seconds to a minute or more allows for desired sanitizing or sterilizing without the need for undesired liquids or alcohols. In this example, the UV light technology is sufficient to kill or reduce viruses, and any present parasitic DNA. Thus, harmful and undesired and harmful germs are cleaned from the hands of a user.

Figure 4:
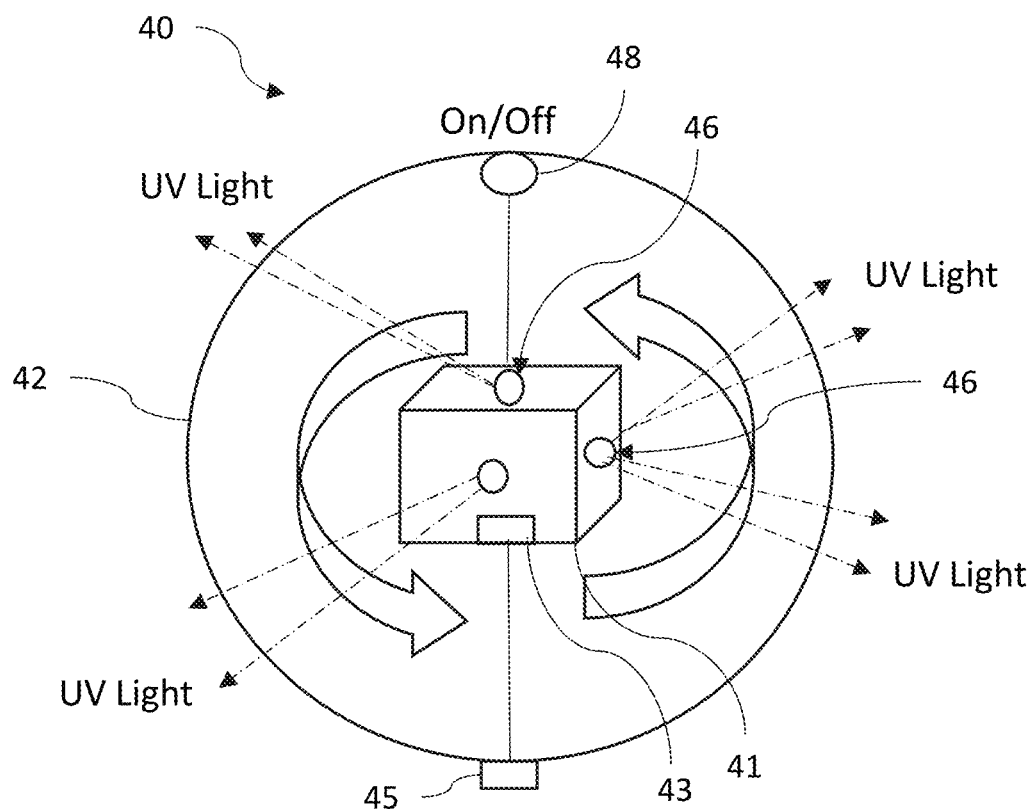
FIG. 4 illustrates an alternative embodiment of a device according to the present disclosure having a rechargeable battery.
Figure 5:
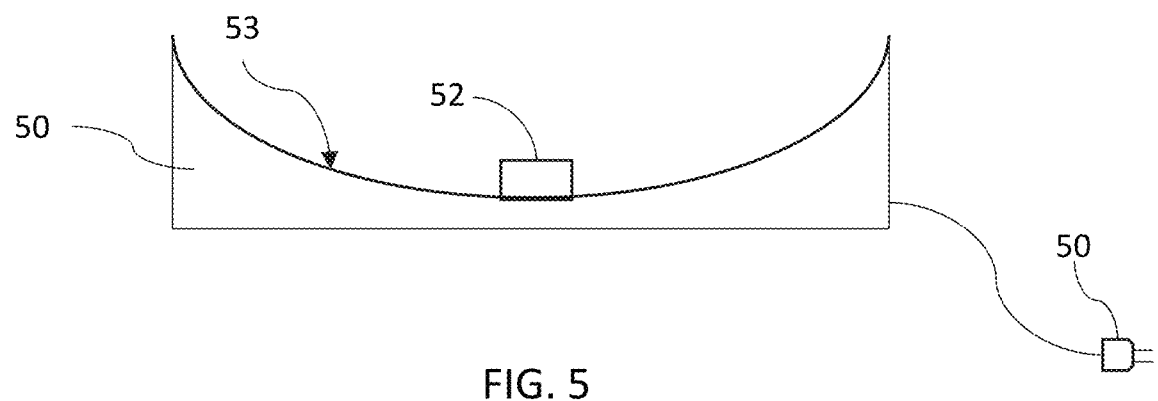
FIG. 5 illustrates an example charging station for charging the battery of FIG. 4.

Referring to FIGS. 4 and 5, in yet another example of the present disclosure, a schematic for an omnidirectional hand sanitizing device 40 is shown. In this example, device 40 includes a glass housing 42 surrounding an internal LED unit 41. LED unit 41 is positioned in the center of housing 42. Housing 42 formed into a sphere to completely enclose unit 41. Glass housing 42 is constructed of a material sufficient to allow UV light to escape and not overly block or refract the emitted light. In one form, glass housing 42 is constructed of quartz glass. In one form, the device 40 defines a diameter of about 1 to 3 inches and in another form the diameter is about 1.5 inches.

LED unit 41 includes a plurality of LED lights 46 positioned in an omnidirectional configuration such that UV light emitting from unit 41 will emit in most or all directions. Accordingly, LED lights 46 are mounted on a structure 47. In this embodiment, structure 47 is a cube having at least one LED light 46 mounted on each side. The LED lights can be any light sufficient to emit UV light out from the glass housing 42 including an example low mercury UV-C LED having a wavelength of about 254 nm. The power requirement can be about 3000 $\mu watt*cm^2/sec$.

Structure 47 includes a power supply or battery 43 to provide power and connectivity to the LED lights 46. Optionally, a circuit board (not shown) can be provided to allow for programmability. Battery 43 is further coupled to an on/off switch 48. The switch 48 is positioned on an exterior surface of glass housing 42 to allow for user access and control of the light emission of device 40. In yet another example, the battery 43 is coupled to a sensor on a circuit board (not shown) that responds to touch as a mechanism to turn on the device 40.

In this example, device 40 further includes a charging port 45 operable to connect to charging stand 50 (FIG. 5). The charging port 45 is coupled to a rechargeable battery 43 and when connected to charging stand 50, allows for the battery to be recharged. Charging port 45 is operable to connect to a receiving port 52 of stand 50. Stand 50 can be plugged into a wall outlet or other power source via USB or otherwise via a plug connector 54. In this example, stand 50 includes a rounded convex mounting surface 53 shaped and sized to receive and nestle the device 40. Although this is schematic, there are various configurations possible for an example charging stand 50 that are contemplated and within the scope of the present disclosure. This includes a more vertical stand, a rectangular or square shaped stand, or even just a charging cord that directly connects with the charging port 45. The device 40 can further be provided in a corresponding carrying case shaped and sized to receive and enclose device 40 while not in use.

Figure 6:
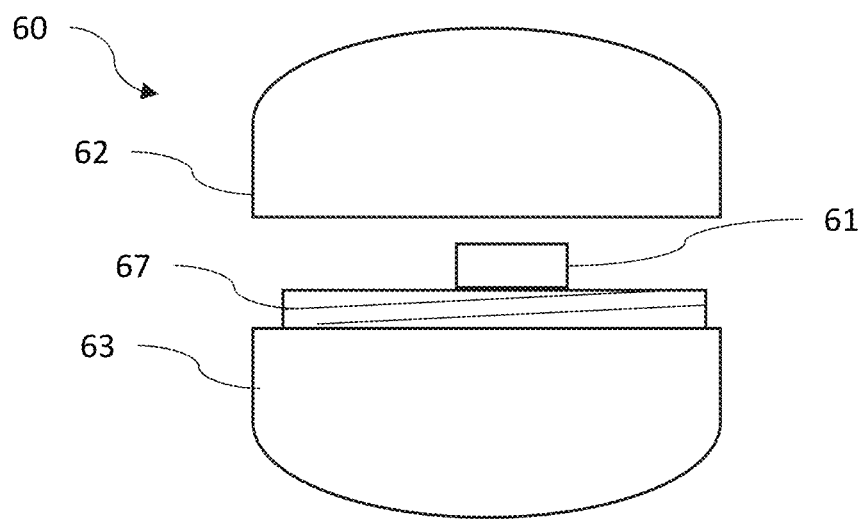
FIG. 6 is a schematic of an example hand sanitizing device separated into two sections having a threaded connection portion.
Figure 7:
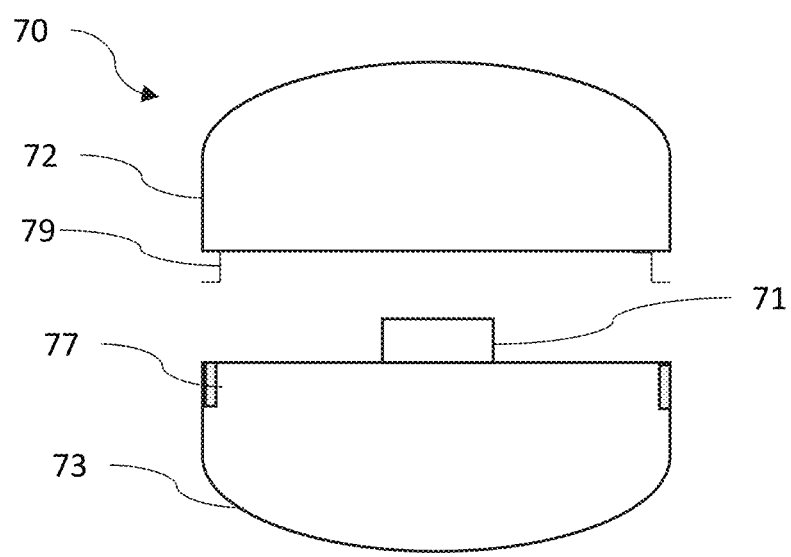
FIG. 7 is a schematic of an example hand sanitizing device separated into two sections having a clip-in connection portion.

With regard to FIGS. 6 and 7, the present disclosure further provides for portable and omnidirectional hand sanitizing devices 60 and 70, each having an internal LED unit 61 or 71, respectively, which are similar to the LED unit described with respect to FIG. 4 and unit 41. Devices 60 and 70 schematically illustrate various mechanisms to access the internal components of the LED units 61 and 71. Device 60 includes a threaded portion 67 which allows separation into two sections, upper section 62 and lower section 63, both still constructed of a suitable glass like quartz. The threaded portion 67 engages with a corresponding thread (not shown) on an interior surface of upper section 62. Accordingly, this allows for a disposable and/or removable battery design and replacement of LED lights when necessary.

As shown in FIG. 7, device 70 can be separated into two sections, upper section 72 and lower section 73, both still constructed of a suitable glass like quartz. Device 70 includes a clip mechanism having a latching portion 77 positioned on a lower section 73. Clips 79 extending from upper section 72 are positioned to engage the latching portion 77 and thus secure upper section 72 to lower section 73 and enclosing the LED unit 71. Accordingly, this allows for a disposable and/or removable battery design and replacement of LED lights when necessary.

Figure 8:
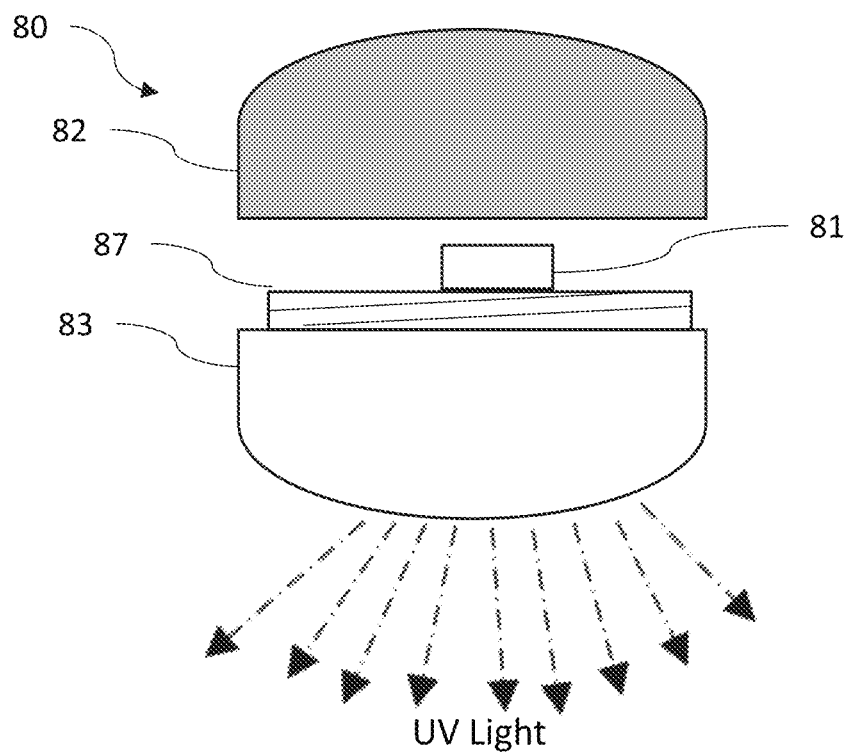
FIG. 8 is a schematic of an example hand sanitizing device separated into two sections having a replaceable section.

Referring to FIG. 8, a further example of a handheld sanitizing device 80 is shown. Device 80 can be separated into two sections, upper section 82 and lower section 83. Device 80 includes any attachment mechanism to connect the upper and lower section, however, in this example, a threaded portion 87 is shown. In this example, only lower portion 83 is constructed of clear glass allowing the emission of UV light therefrom. Upper portion 82 is constructed of a different material which can be disposable, interchangeable, defining a non-clear color, or otherwise. An LED unit 81 is mounted therein which includes one or more UV emitting LED lights. In this example, the LED lights can be configured to only emit in the direction of lower section 83. This allows for the constructing or manufacturing of multiple units having various benefits. For example, upper section 82 can include promotional material or customized graphics. This further allows for a disposable and/or removable battery design and replacement of LED lights when necessary.

Figure 9:
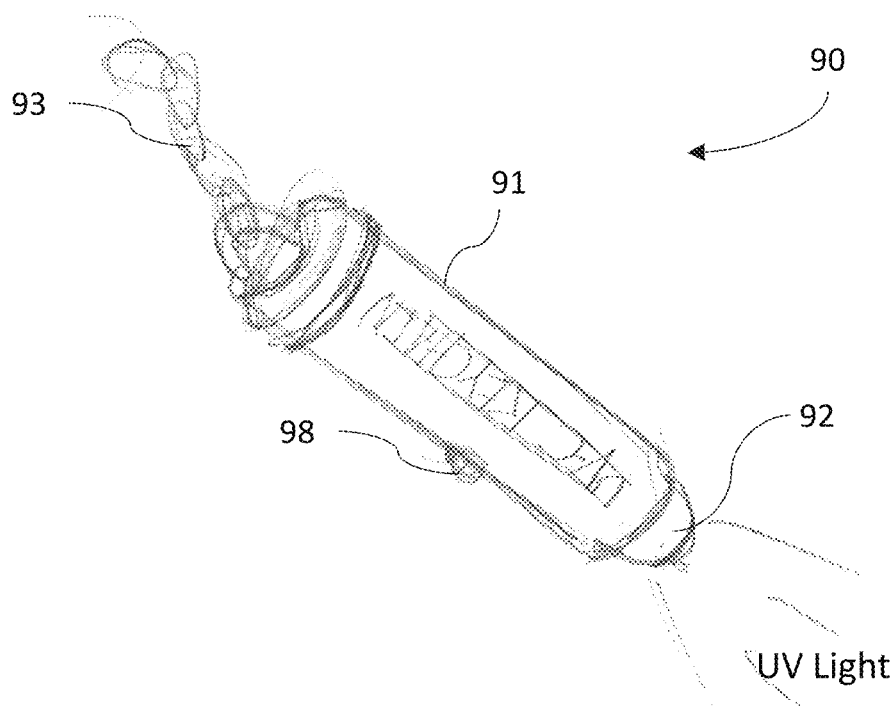
FIG. 9 is an example keychain UV light emitting hand sanitizing device.

Referring to FIG. 9, a further example of a hand sanitizing device 90 is shown. In this example, device 90 is a keychain device having a main body 91 for housing internal components such as a battery. An LED unit 92 for emitting UV light is positioned at a distal end of the body 91. Device 90 includes an on/off button 98 and a chain portion 93. Chain portion 93 is operable to connect to keys or the like and thus forms a portable and convenient hand sanitizing mechanism for a user.

The portability of the keychain device 90 allows for a wider range of applications. The wireless and handheld design allows for a simple and efficient application of UV-C light. For example, the UV light source 92 may sanitize a surface for procedures such as obtaining blood cultures or orthopedic prosthesis prior to insertion into the body. If a large UV-C device were used, a patient would have to be manipulated or moved into position to receive the therapeutic light. Thus, increasing the risk of falling or injury, especially if a patient is sedated. The handheld device 90 avoids this risk by bringing the therapeutic light to the patient and providing quick application without significant manipulation of a patient's position.

The maneuverability of device 90 allows for precise application of UV-C light. UV-C light at a wavelength of 222 nm has been shown to effectively kill bacteria and other microorganisms while not even penetrating the outer layer of the human skin or the human eye. In one example, the LEDs may be configured to emit UV-C light at about 222 nm and the device 90 is then used by bringing the device into close proximity to an eye or tissue and directing the UV-C light source toward the treatment surface. The UV-C light provides sanitation on the surface of the eye in ophthalmological procedures or treatment of conditions such as conjunctivitis without damaging or irritating an eye.

Figure 10A:
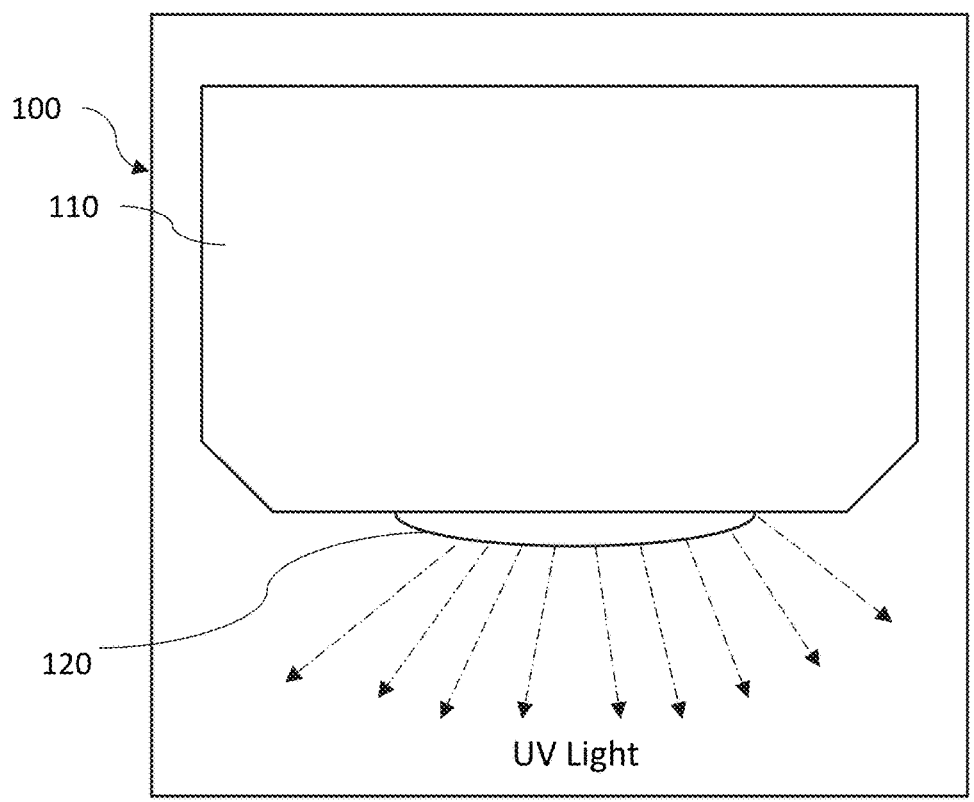
FIGS. 10A and 10B illustrate a front face and side view, respectively, of a wall mount UV light emitting hand sanitizing device according to the present disclosure.
Figure 10B:
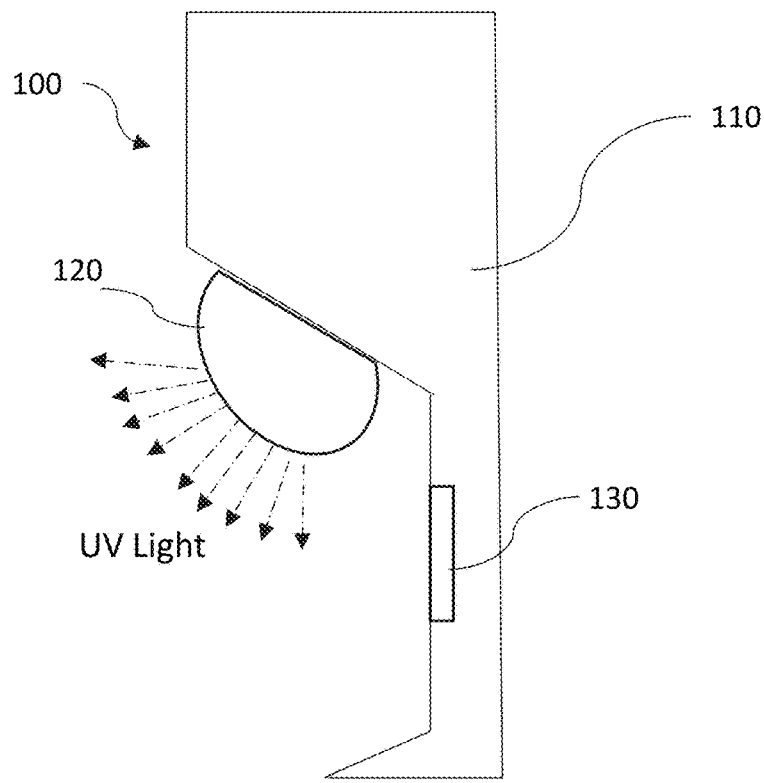
Figure 11:
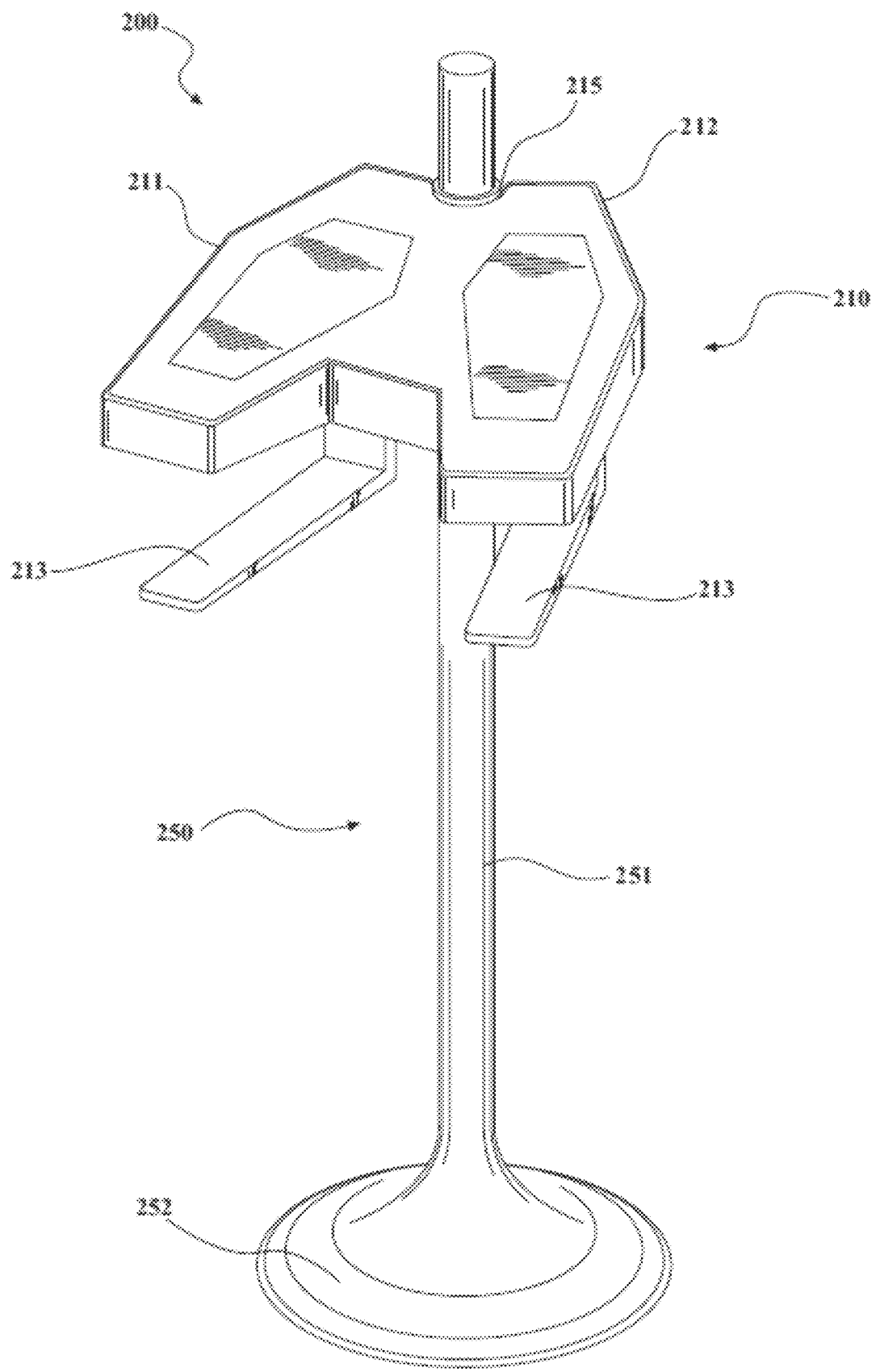
FIG. 11 illustrates a perspective view of a standalone hand sanitizing apparatus with a housing having LEDs emitting UV-C light.
Figure 12:
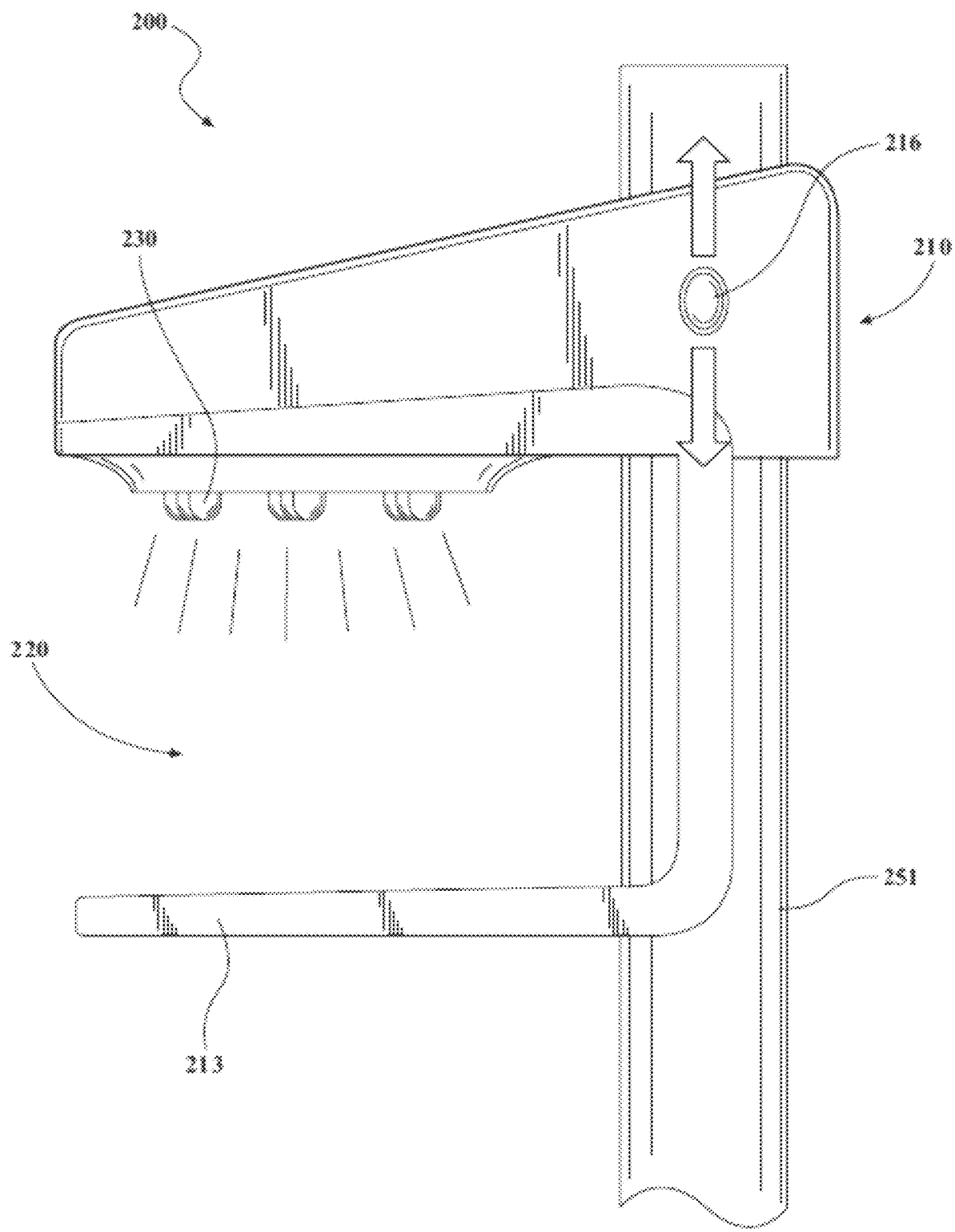
FIG. 12 illustrates a side view of the standalone hand sanitizing apparatus of FIG. 11.
Figure 13:
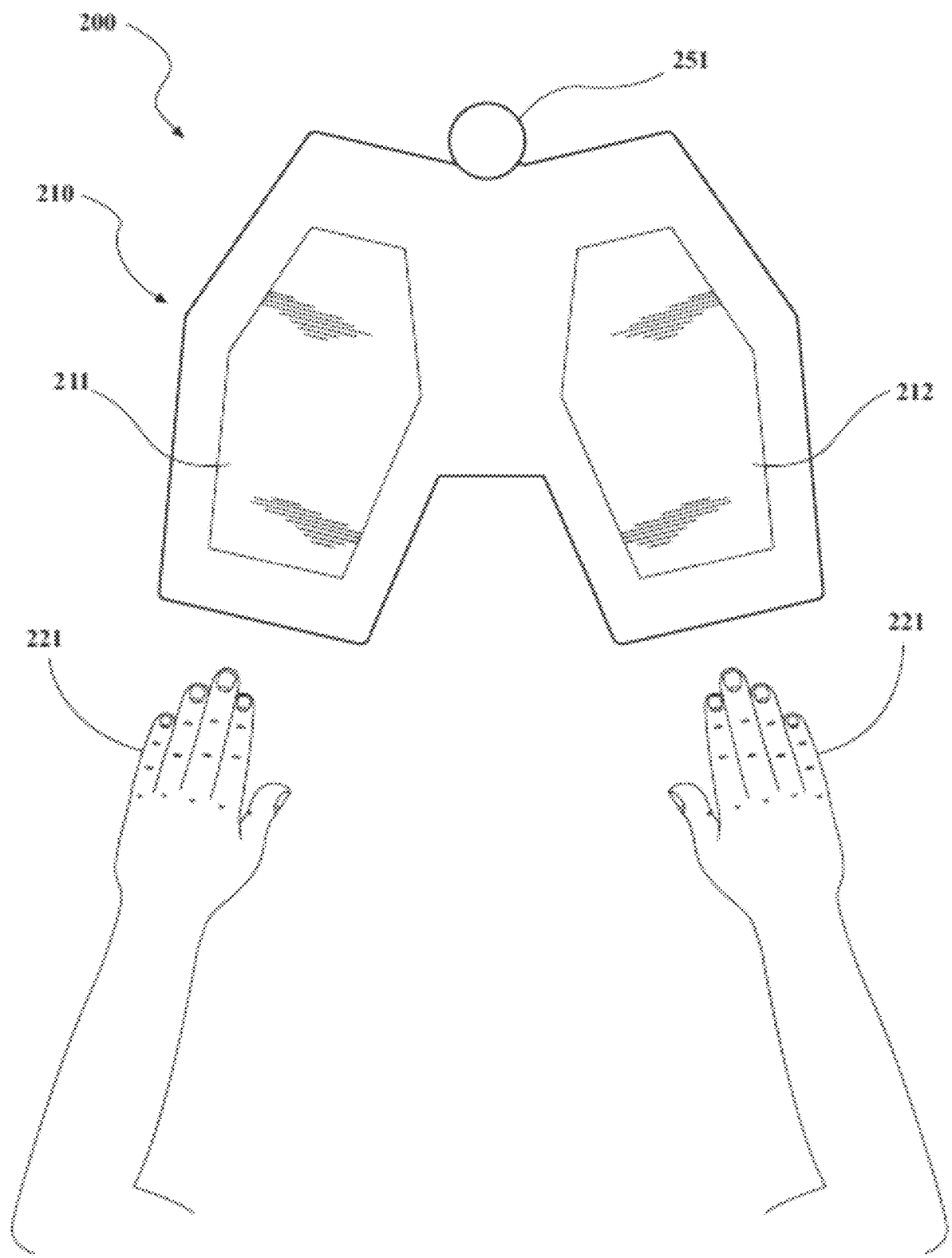
FIG. 13 illustrates a top view of the standalone hand sanitizing apparatus of FIG. 11.
Figure 14:
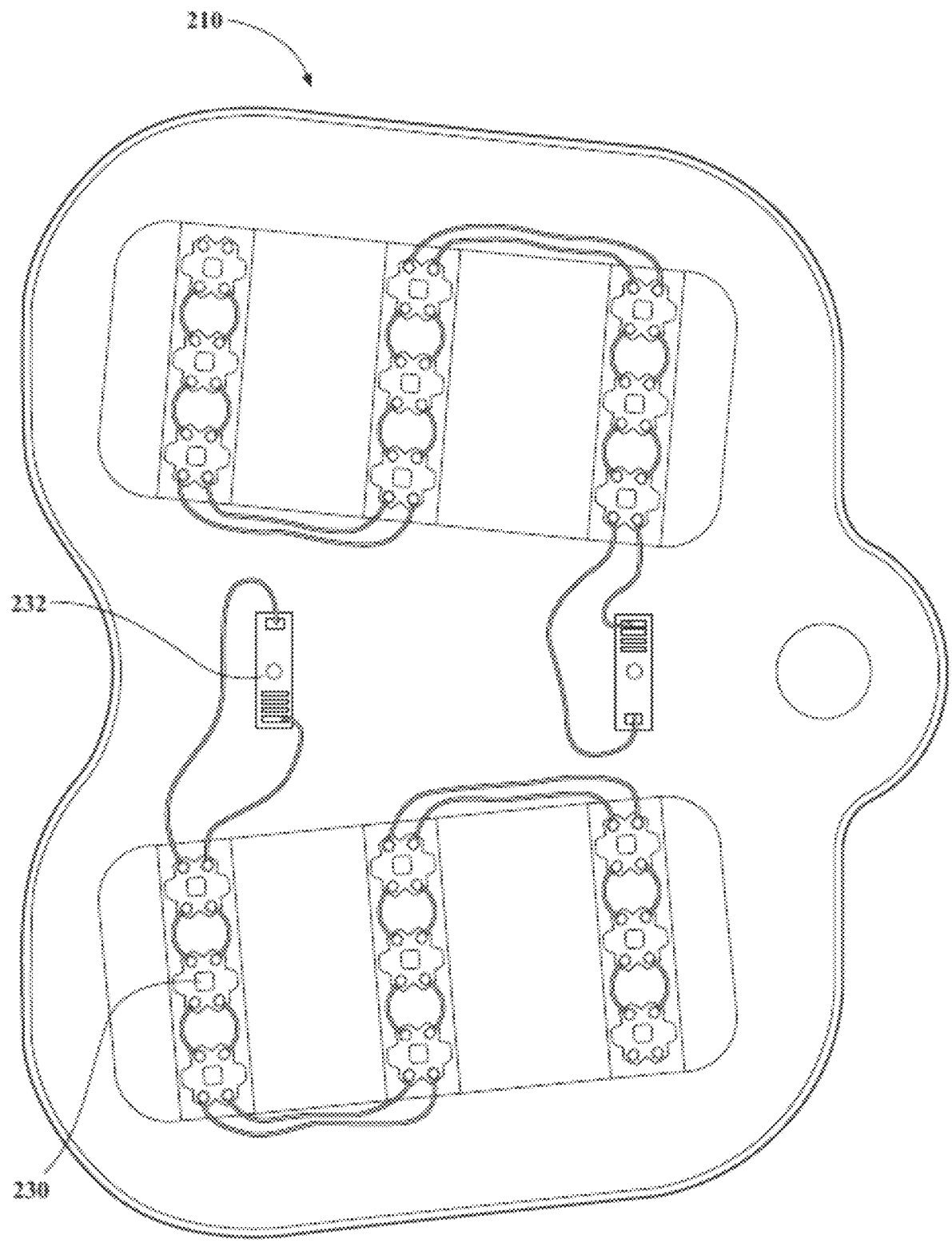
FIG. 14 illustrates an underside of the housing showing UV LEDs connected to a power source and arranged in rows on the right and left sections of the housing.

Referring to FIGS. 10A-10B, the present disclosure provides for a wall mount UV apparatus 100 operable for sanitizing hands placed in a UV light exposure area. The device 100 includes a housing 110 operable to be mounted onto a wall or surface. A UV emitting device 120 is positioned and mounted within the housing but at least partially exposed. Device 120 can be any of the previously described hand sanitizing devices like device 10, 40, 60, 70, and/or 80, so long as a portion the device allows for UV light emission. In this example, the device 120 is positioned to emit light in a relatively downward angle and thus allows a user to place hands below the device 120 to kill any germs or otherwise while in use. Device 120 can be electronically coupled to a power source and optionally to a sensor 130. Sensor 130 can be any motion sensor operable to turn on the LED lights of device 120 when an object is present.

Referring to FIGS. 11-17, the present disclosure provides for a standalone UV-C sanitizing apparatus 200 operable for sanitizing hands placed in a preset UV-C light exposure area. The standalone apparatus includes a housing 210. In this example, housing 210 is configured with left section 211 and right section 212, primarily to indicate the placement of a left and right hand and form two distinct areas of exposure.

In an example, handguards 213 are positioned below housing 210. The handguards 213 can be connected to and extend from housing 210 downward a desired distance sufficient to allow a user's hands to fit below the housing 210 and above handguards 213. Handguards 213 then extend out and towards a user, substantially parallel to a plane of the housing 210. This forms an open space for placement of a user's hands. The distance between the handguards 213 and the housing 210 should allow for the user to position their hands at an optimal distance from the LEDs within a preset or desired exposure area for effective sanitization such that the user can rest their hands on or above the handguards 213. In an example, the effective distance a hand should be from the LEDs can range from 2 inches to 6 inches. In this example, the LEDs are positioned on essentially the same plane to provide for even light emission and distribution within the exposure area. Accordingly, the housing can also be planer.

The distance of the handguards 213 can be repositioned to adjust the amount of distance between the user's hands and the LEDs based on the power output of the LEDs and the desired killing effect. Further, the amount of time that the hands should be left under the LEDs is proportionate to the power output of the LEDs and the distance of the LEDs to the hands, i.e. the greater the power output, the shorter amount of time is needed under the UV light and the shorter the distance of the hands to the LEDs, the shorter the amount of time is needed under the UV light.

The LEDs are configured to emit UV-C light, which has ranges in wavelengths from 100 nm to 280 nm. UV-C light has the natural property of killing germs, including killing bacteria and disabling viruses. UV light in many forms is harmful to human skin and human eyes, however, when used properly, UV-C light can safely kill and disable germs on human skin without causing any damage or irritation. Specially, UV-C light at a wavelength of 222 nm has been shown to effectively kill bacteria and other microorganisms while not even penetrating the outer layer of the human skin or the human eye. In an example, the LEDs are configured to emit UV-C light at a wavelength of about 222 nm. Moreover, UV-C light can be effective in sanitizing and disinfecting surfaces and materials like personal protective equipment (PPE) like gloves, masks, and gowns. This can be especially useful during times of equipment shortages, like a pandemic, by providing a process to reuse single-use or disposable equipment.

LEDs have many advantages over other light sources, including lower energy consumption, longer lifetime, improved physical robustness, smaller size, and faster switching. In an example, handguards 213 are positioned 3 inches away from LEDs 230 and the user is directed to leave the hands under the light for at least 5 seconds to 60 seconds and more specifically for at least 6 seconds to 30 seconds and yet further for 6 seconds to 10 seconds. Apparatus 200 can be equipped with indicia like a timer or a light indicator to convey to the user that the sufficient exposure time has been met. This can be done in a variety of ways, including multiple "percent clean" indicator such as 10% clean, 50% clean, 70% clean, complete. Moreover, the apparatus can simply turn off when the preset time for emission time has surpassed. The amount of time left under the UV light can also be proportionate to the targeted bacteria, virus, or other microorganisms.

In an example, LEDs 230 are provided in each of the left section 211 and right section 212 and positioned on an underside of each section to emit downwardly towards handguards 213. Each LED is configured to emit UV light. The standalone apparatus 200 includes a vertical stand 250. Vertical stand 250 is includes a pole or post 251 and a base 252. In an example, base 252 is partially spherical-shaped and funnels upwards into pole 251 forming a balanced vertical stand 250. Pole 251 is configured to adjustably mount housing 210 whereby pole 251 engages with aperture 215 of the housing 210. Housing 210 can then be adjusted up or down to the desired height above the ground.

The present disclosure provides for a standalone UV-C sanitizing apparatus 200 operable for sanitizing hands placed in a UV-C light exposure area 220. LEDs 230 are positioned on the underside of housing 210 for light exposure downward. Handguard 213 is positioned below the housing 210 and creates the light exposure area 220. Users can place their hands into the exposure area 220 for effective disinfecting/sanitizing. In an example, an adjustable fastener 216 can be positioned on the side of housing 210. When the housing and handguard 213 are positioned at the desired positions creating the desired distance of UV-C light exposure area 220, the adjustable fastener can be positioned in the locked position so as to lock the housing 210 at that position. The housing can be adjusted by disengaging the adjustable fastener, moving the housing to the desired height, and re-engaging the adjustable fastener to the locked position.

The distance of UV-C light exposure area 220 can be adjusted to be greater or smaller depending on the desired LED power output and the intended exposure time of the UV-C light to the user's hand. In this example, the apparatus 200 is positioned to emit light in at a downward direction whereby a user can place hands 221 below the housing 210 to kill any germs or otherwise while in use. Housing 210 can be electronically coupled to a power source (not shown). In a further example, apparatus 200 includes a sensor including a motion sensor to activate the LED lights of apparatus 200 when an object or hand is detected, i.e., is present. The sensor can be configured to operate for a preset length of time corresponding to the distance from the LEDs and the intensity of UV-C light exposure area 220. On an underside of housing 210, LEDs 230 are configured to emit UV-C light.

It is understood that people have varying degrees of hand sizes and thus the surface area of a given user can vary drastically. The arrangement of LEDS corresponds to a cover an exposure surface area sufficient to disinfect/sanitize most hand surfaces. In this example, LEDs 230 are arranged in three rows on the left section 211 and right section 212 of housing 210. Three LEDs are positioned in each row for a total of nine LEDs in each of section 211 and section 212. Each LED 230 is connected to power source 232. In an example, power source 232 is a disposable battery. In yet a further example, power source 232 is a rechargeable battery. The LEDs are connected to a power source in a manner so that each LED can be replaced without causing a failure in the circuit and thus, failure of one, two, three or possibly more LEDs does not reduce the overall effectiveness of apparatus 200.

Each LED 230 is coupled to a circuit board which is powered by power source 232. In an example, each LED corresponds to a single designated circuit board which is then coupled to a controller for programming. In another example, the LEDs are provided with wire pigtails that poke through holes in a single circuit board. It is further within the scope of the present disclosure that each row of LEDs is mounted to a corresponding circuit board and all the circuit boards are then connected to a controller or a basic on/off switch. A Lithium (Li+) ion battery or equivalent can be used, however, disposable alkaline and/or other rechargeable batteries are within the scope of this disclosure. A power switch is coupled to the circuit board(s) to activate the LEDs 230. In this example, each LED 230 can be adapted to receive a current of about 20 mA and a power consumption of about 70 mW while delivering UV light having a wavelength in the range of between about 100 nm and 290 nm, 200 and 250 nm, 220 and 230 nm, around 220 to 227 nm, and between 254 nm and 265 nm. In yet another example, the device includes a safety circuit that will identify when and if an individual LED "burns out" or ceases to function for any reason. Since most UV-C LEDs do not emit visible light, a colored light LED can be included in the device to let a user know that the device is on and operating (i.e., disinfecting).

The present disclosure provides for a method of sterilizing/sanitizing hands of a user by providing an apparatus 200 having a plurality of UV-C emitting LEDs 230 and activating the LEDs 230 to emit the UV-C light from a housing 210 to expose a user's hand to the UV light. In an example, the LEDs are configured to emit UV-C light at a wavelength of about 222 nm in order to safely kill germs without irritating or damaging the human skin or eyes. In use, for example, a user may turn apparatus 200 on by pushing on/off button and thus activating the LEDs 230 to emit UV-C light. In another example, apparatus 200 is turned on by motion sensors that detect and activate upon movement under the device. Once the apparatus 200 is activated, the user positions hands 221 on or just above handguards 213 and exposes the hands to the UV-C light by placing the right hand under right section 212 and the left hand under left section 211. After a preset length of time, the user will flip over hands 213 to expose the other side of the hand to LEDs 230. In an example, the apparatus is equipped with indicators that convey to the user when it is time to flip over the hands and when the sanitizing is complete. Placing one's hands under apparatus 200 for several seconds to a minute or more allows for desired sanitizing or sterilizing without the need for undesired liquids or alcohols. In this example, the UV light emission is sufficient to kill or reduce viruses, and any present parasitic DNA. Thus, harmful and undesired and harmful germs are cleaned from the hands of a user. In a further example, this apparatus is configured to kill coronavirus. A similar process is effective for sterilizing/sanitizing/disinfecting PPE including gloves, masks, and gowns.

The present disclosure further provides for a method of sterilizing/sanitizing PPE such as disposable protective gloves, reusable protective gloves, masks, and gowns. In this example, apparatus 200 can be used to clean undesired and harmful germs on protective gloves. Protective gloves protect the user from harmful germs, bacteria, and viruses from the environment. However, once the germs, bacteria, or viruses attach to the gloves, the gloves are compromised and can lead to the user self-infecting or infecting others. Typically, the user would need to either dispose of or wash the compromised gloves to protect and avoid future infections or contaminations. In this example, the user can position the hands with the protective gloves under apparatus 200 whereby the motion of the hands activates the plurality of LEDs 230 emitting UV light from a housing 210 to expose a user's gloves to the UV light. The UV light is emitted at a wavelength that is sufficient to kill or reduce viruses, and any present parasitic DNA. Thus, harmful and undesired and harmful germs are cleaned from the protective gloves of a user. In a further example, this apparatus is configured to kill coronavirus. This method of sterilizing/sanitizing protective gloves reduces waste and minimizes costs by allowing for multiple uses of disposable protective gloves and reduces the washing of compromised, reusable protective gloves.

Figure 15A:
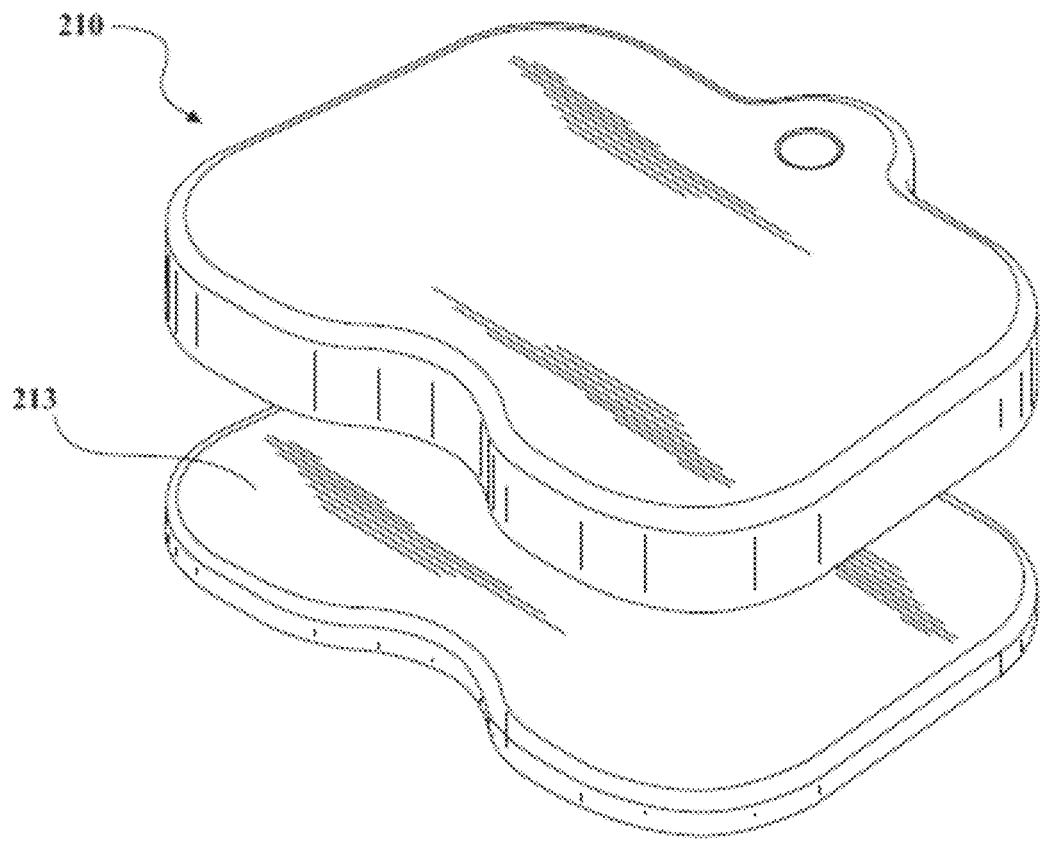
FIGS. 15A and 15B illustrate a schematic perspective and a cross-sectional view, respectively, of a standalone hand sanitizing apparatus with a housing containing LEDs emitting UV-C light.
Figure 15B:
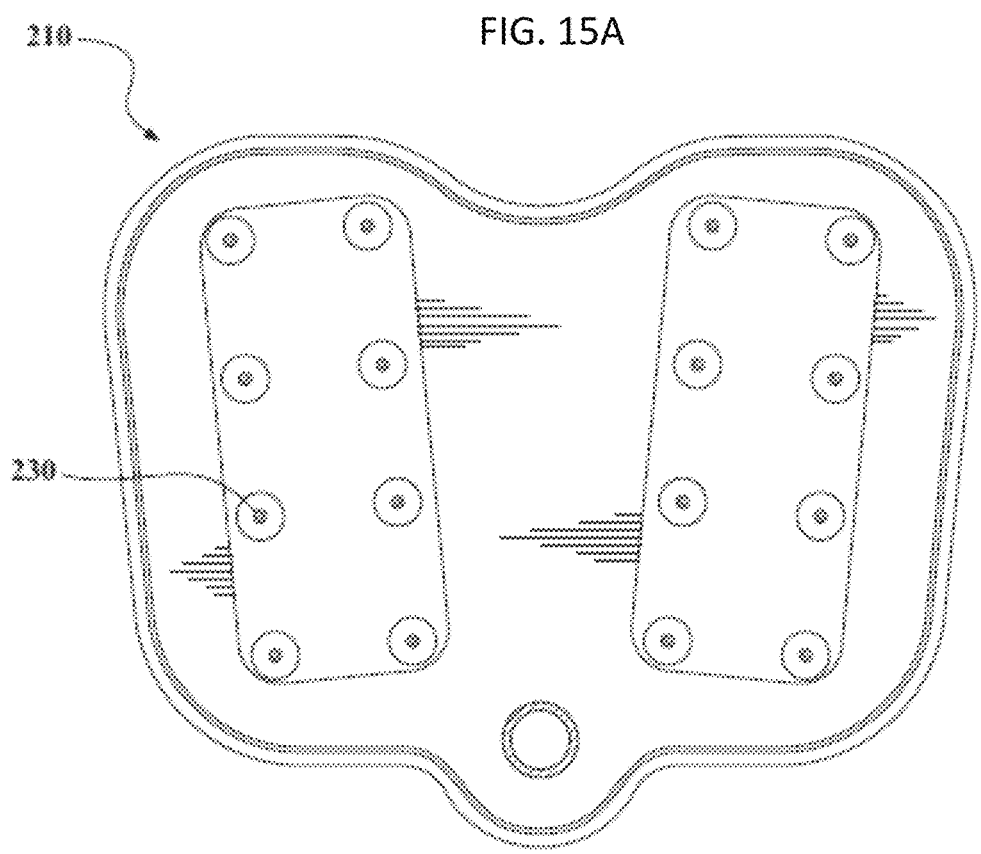

In the examples of FIGS. 15A and 15B, the present disclosure illustrates a perspective view and a cross-sectional view of a standalone UV-C hand sanitizing apparatus 200 with a housing 210 and a reciprocal handguard 213. LEDs 230 are positioned on the undersides of the left section and right section of the planar housing. In this example, two LEDs are placed in four rows in each of the left section and right section of the planar housing. Hands are placed between the housing and the handguard. The user is directed to rest the hands just above or on the handguard to properly position the hands at the desired distance from the LEDs. The user is instructed to flip the orientation of the hands after a predetermined amount of time. In an example, the user is directed by an indicator light to flip the orientation of the hands and to remove the hands once the disinfection is complete.

Figure 16:
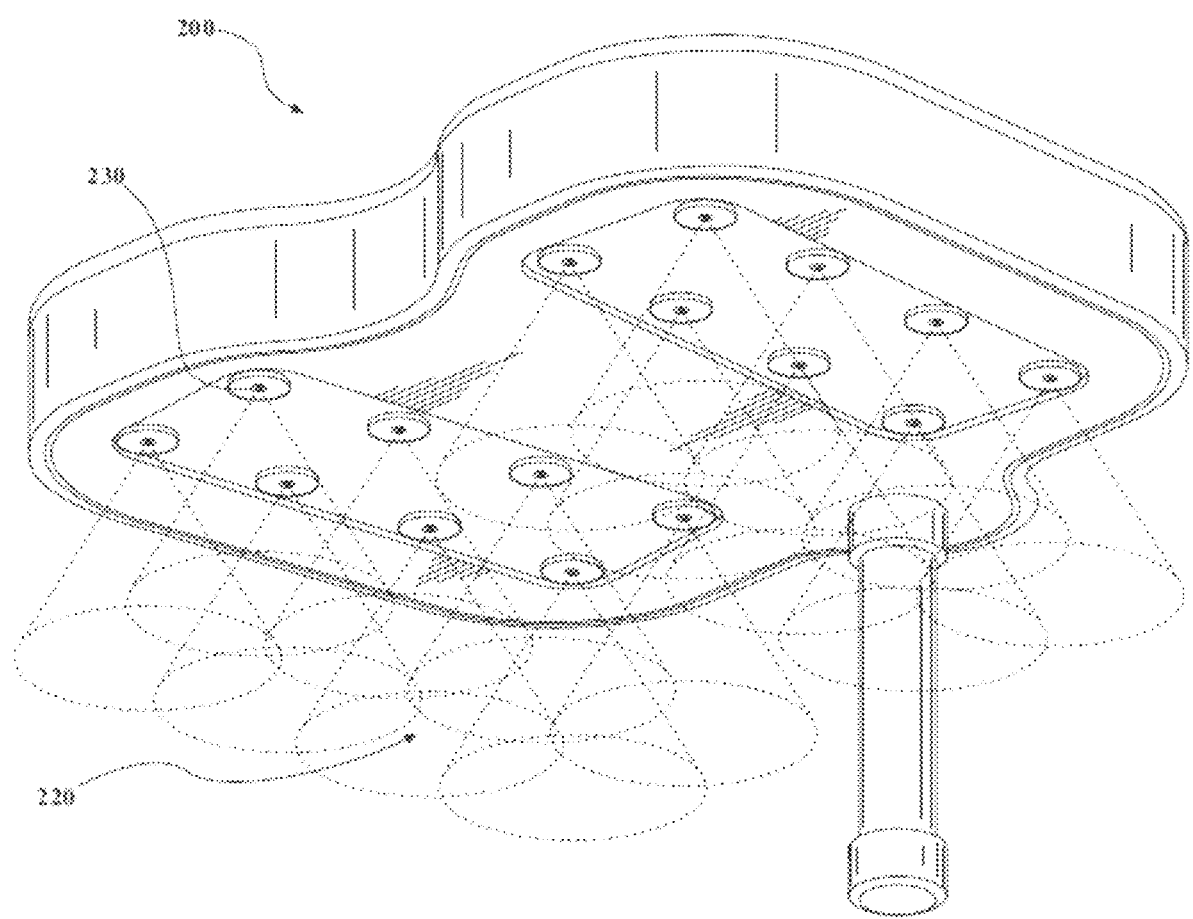
FIG. 16 illustrates a perspective view of a standalone hand sanitizing apparatus illustrating a cone visualization of UV emittance.

Referring to FIG. 16, the present disclosure provides a perspective view of the housing. In this example, two LEDs are positioned in four rows on each of the underside of the left section and right section of the planar housing. Each LED emittance of UV-C light is illustrated by cones that as the cones expand, cover a greater surface area, however, weaken in strength. The arrangement of the LEDs 230 is configured to have cone area crossover sufficient to cover a human hand. In an example, the surface area covered by the cone cross over area within a sufficient power zone for killing microorganisms is sized to cover a surface area of a 95$^{th}$ percentile of human hands. The closer to the LED, the more concentrated the UV-C light. On the contrary, the further away from the LED, the less concentrated the UV-C light, but the light covers more area. The LED lights are arranged so that there is overlap, or redundancy, of the UV-C light. In the event that one or two of the LED lights burns out or malfunctions, the apparatus will still function to disinfect hands because the area that is missing from the malfunctioning LED will be covered by the redundancy of a nearby, functioning LED. The LEDs are connected to a power source in such a way so that if one LED is malfunctioning, then the remainder of the LEDs down the chain are not disrupted by the malfunctioning LED. The malfunctioning LED can then be replaced with a new LED on an individual basis.

Figure 17:
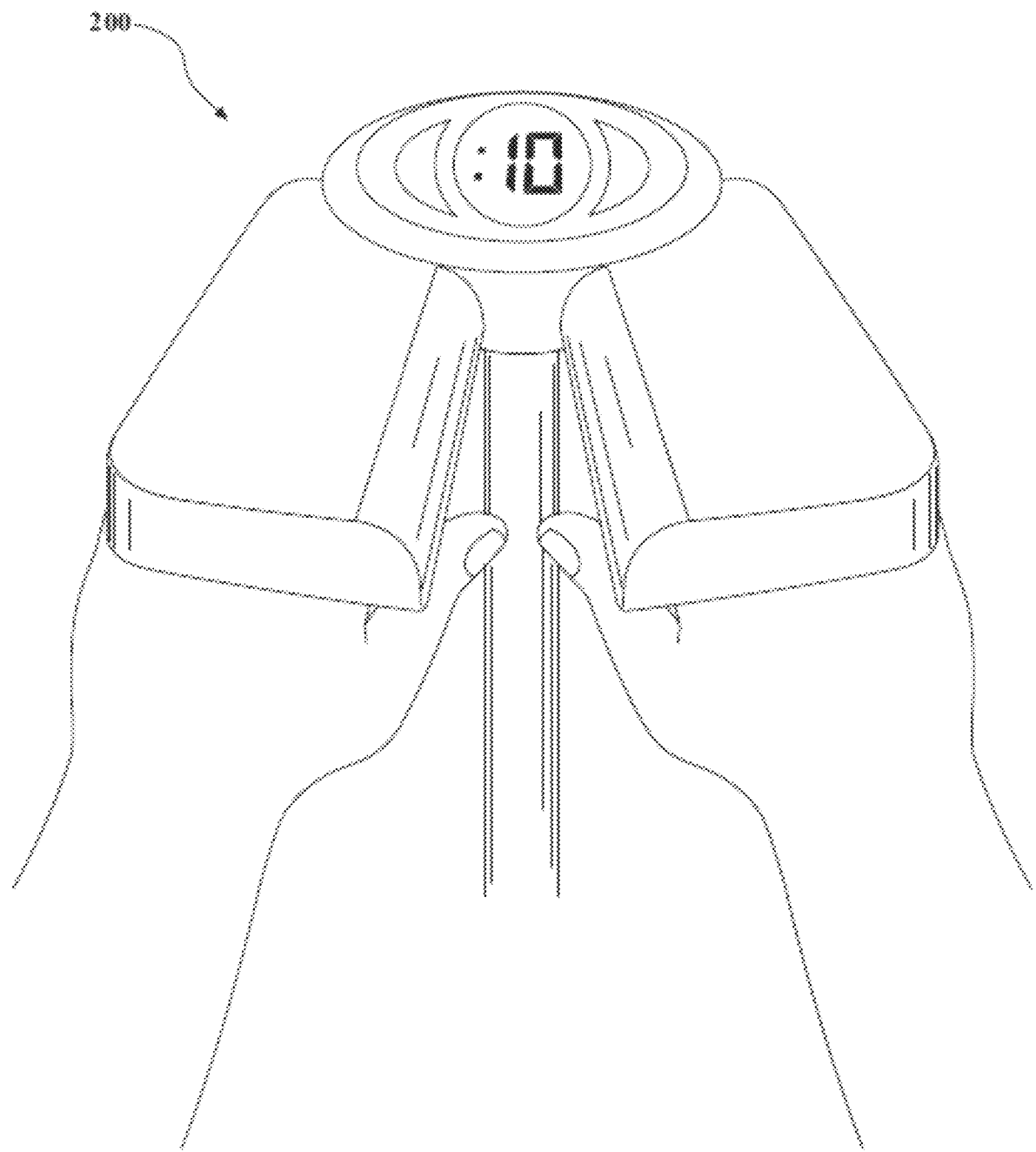
FIG. 17 illustrates a front view of a standalone hand sanitizing apparatus sanitizing a user's hands.

Referring to FIG. 17, the present disclosure provides a front view of the standalone hand sanitizing apparatus disinfecting hands. The apparatus is configured to allow the user to place the hands under each the left section and right section of the planar housing. The user is directed to place the hands directly above the handguard below the planar housing. In an example, the LEDs on the underside of the planar housing is connected to a motion sensor. When the motion sensor is triggered by the hands being placed under the planar housing, the LEDs turn on and emit UV-C light on the user's hands. In a further example, a timer is synchronized with the motion sensor and alerts the user the amount of time that the hands need to remain under the UV-C light to properly disinfect. In a further example, the timer is configured to alert the user when the hands should be flipped over to disinfect the other side of the hands. In yet another example, LEDs are positioned to emit upwards and downwards to simultaneously sanitize both sides of a human hand. Precautions should be taken in a design of this two-way LED emission apparatus to protect a user's eyes, such as physical obstructions or mounting the LEDs deeper within a cavity or space between handguards and the housing to prevent light escape.

Figure 18A:
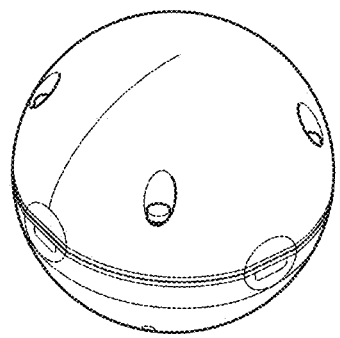
FIGS. 18A-18C illustrate another example of a handheld orb UV-C device having a partially truncated section for illumination.
Figure 18B:
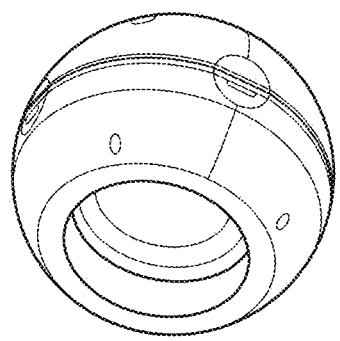
Figure 18C:
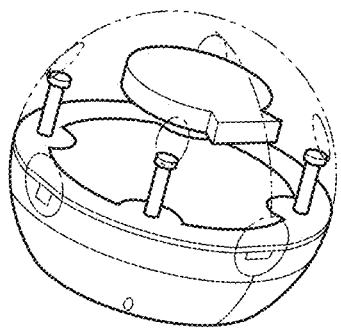

Referring to FIGS. 18A-18C and 19A-19B, and 20A-20B, a further example of a handheld device is shown. In FIGS. 18A-18C, the device is shown schematically to illustrate assembly and internal components. In this example of a partial orb has a mostly spherical shell that can be manually held and handled by a user. In a further example, various indentations are positioned around an outer surface of the orb to facilitate more effective handling and gripping by a user. A portion of the orb is truncated or cutout to define a relatively flat portion and thus exposing inner LEDs that emit UV-C light therefrom. As shown in FIG. 18C, the outer shell is schematically shown as transparent to reveal internal components like a circuit board for mounting individual LEDs positioned to emit UV-C light outward from the cutout section. In this example, the outer shell portions can be fabricated from plastic or 3D printed and formed as a modular assembly. This can make for adding or replacing internal components more convenient.

Figure 19A:
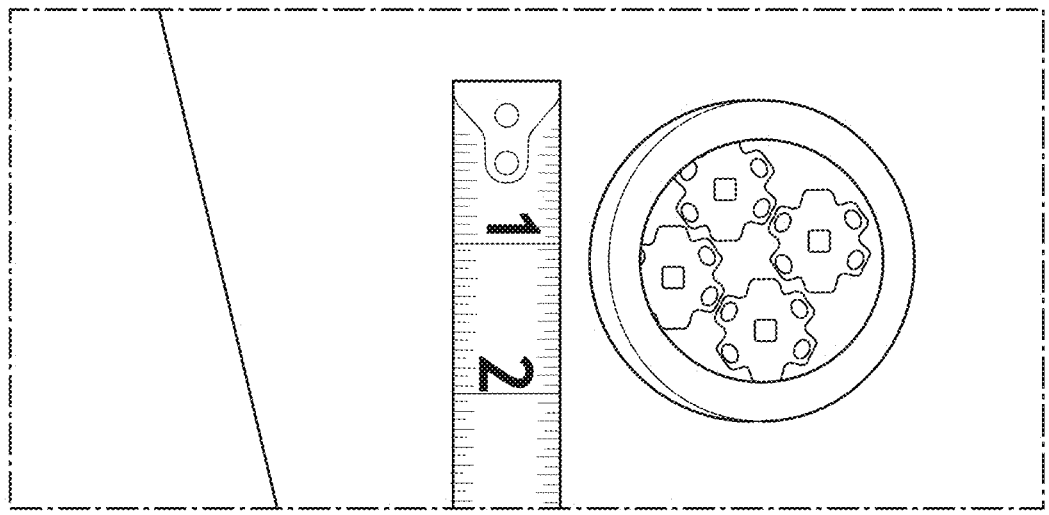
FIGS. 19A-19B illustrate a hemisphere device having a relatively flat illumination section.
Figure 19B:
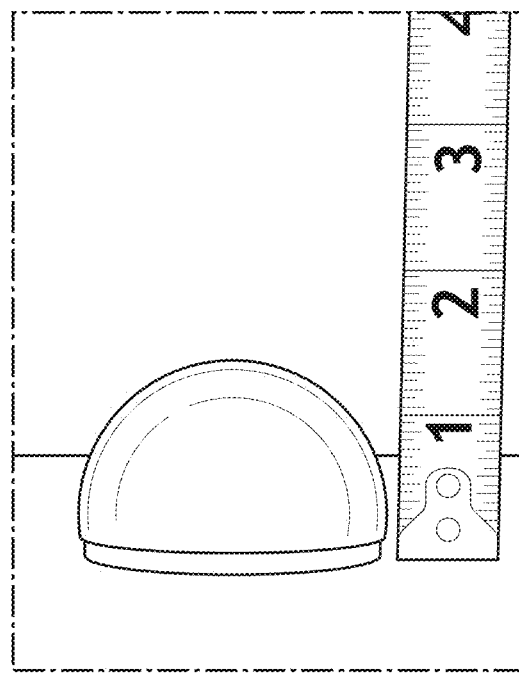

FIG. 19A-19B illustrate a hemisphere design with a relatively flat half section having a plurality of LEDS (4 in this example) mounted within an opening of an outer shell that are configured to emit UV-C light therefrom. In this example, the outer shell can be 3D printed or manufactured using a mold. The depth of the hemisphere (also the radius) can be 1 to 2 inches as shown in the exemplary photographs. In an example, a transparent window is provided to allow for exposure without being able to physically touch the LEDs without opening the device.

Figure 20A:
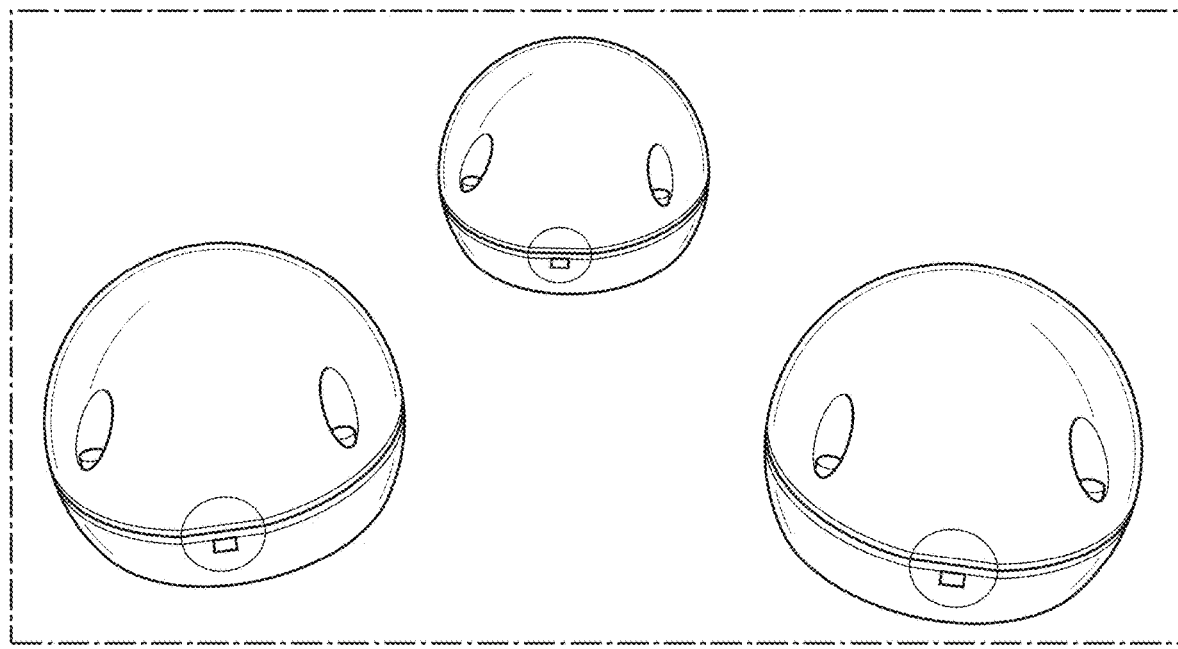
Figure 20B:
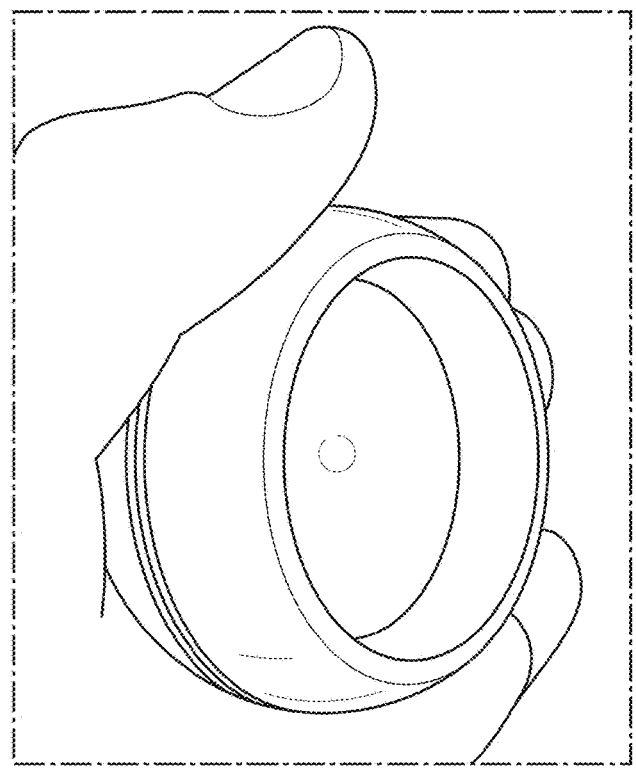

The device shown in FIGS. 20A and 20B are directed to an example for partially orb enclosures which may or may not be plastic that can be 3D printed if desired. In an example, an equator grooved line is formed along a perimeter of the enclosure or having a light transmitting component added to transmit light that is colored and not UV-C. This light can be turned on to indicate the device is on. In an example, these indicator lights are fluorescent. In another example, the indicator light, which is not UV-C is positioned on the same plane as the UV-C lights and turns on when the device is on to allow a user to know that the device is emitting UV-C light. In even another example, a different indicator light (a different color for example) illuminates the device to indicate if the device is hot and needs time to cool.

Figure 21:
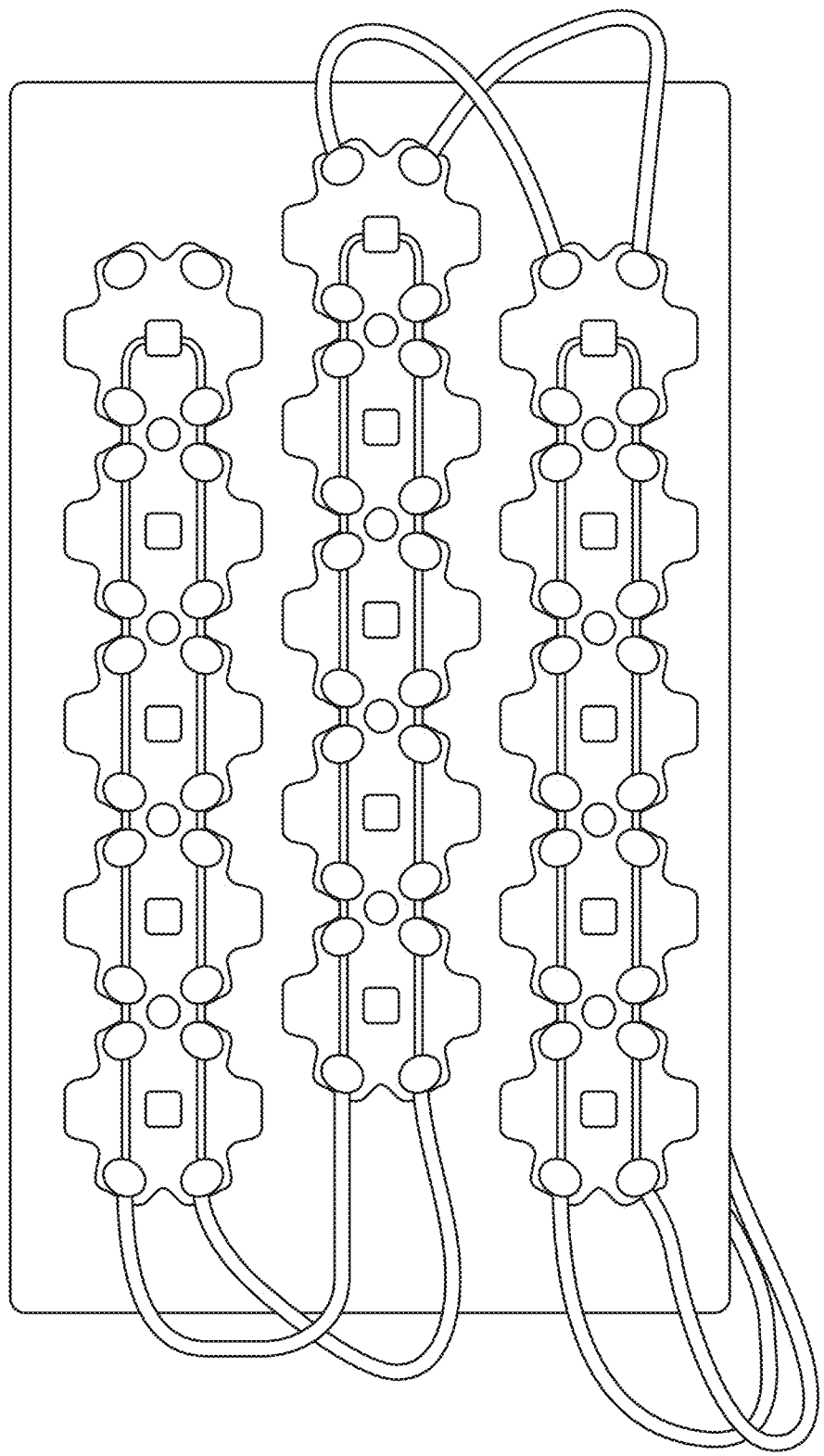
FIG. 21 illustrates a printed circuit board with a plurality of UV-C LEDs.

FIG. 21 illustrates an example printed circuit board with a plurality of LED's mounted thereto and wired together to allow for emission of UV-C light therefrom. This can be incorporated into any device designed for sanitizing skin or a surface. In this example, 15 LEDs were mounted on a board connected to a battery case. In one example, eight AA batteries were used, which generated 12V to power the LEDs. The arrangement of the UV-C LEDs is configured to allow for generating cones of exposure to ensure effective killing of microbials and undesired germs within a distance or proximity to the LEDs when the device is on.

Exemplary advantages and improvements for an "orb" or "ball" or "spherical" design include but are not limited to:
1) Transparent spherical quartz glass encasement/enclosure.
2) Quartz encasing on a partial or fully spherical orb design allows for a user to roll over skin as it emits light omnidirectionally. The LEDs can be mounted in a way that sets a distance that prevents error for effective sanitization and UV-C exposure from other units.

3) Rechargeable battery.
4) The encasing can be a reinforced structure for strength and durability that also mounts an internal center unit having LED's and a rechargeable battery or access to a power source for charging.
5) Aesthetically pleasing designs are available.
6) In a further example, other colored light emitting diodes can be provided for indicia of on and off and for preference of appearance of device; i.e. blue, pink, purple with or without fluorescence, etc. This can be used as safety to indicate that the device is hot and needs to cool. For example, a unit can be configured to include a light that glows (e.g., red) to indicate that it is on. The light can run along a rim. In another example, a light can also emit, like blue light, from the same plane or close plane to the UV-C LEDs to indicate that the device is on.
7) A rechargeable case can be made available as well with various color options.
8) The device can include a rechargeable step-down low voltage cord and system.
9) The device can be used for almost any part of human skin but should be careful to avoid exposure to mucosal and open wound exposed areas.
10) The device can be used over gloves as well as any other surface that safely tolerates UVC emission.
11) The device can be left on in a user's pocket for a few seconds and it can disinfect that too; however, safety features can also be included to prevent this from occurring and eliminate any risk from overheating or over-exposure.
12) With quartz, the device can be made to be water resistant or waterproof.
13) The device can further include a carrying case and it can clean its own carrying case; just leave on for a short time.
14) The device uses UV-C solid state technology that uses UV-C light preferably in the far UV-C range. Our spectrum will 190 nm to and option up to 280 nm of wavelength in the ultraviolet spectrum.
15) On off switch with safety mechanism—child proof option.
16) Can be used on pets.

Exemplary advantages and improvements for a half sphere "orb" or "ball" or "spherical" design include but are not limited to:
1) Similar advantages as discussed above.
2) Easy to use with exposure and emission of UV-C light in the same direction or partially omnidirectional.
3) The outer shell can be made to include silver oxide or copper which is bacterial static and antimicrobial naturally.
4) Personal device that can be carried on person that can disinfect other objects and surfaces.
5) Fluorescent color emitting options.

Exemplary advantages and improvements for a key chain design as shown in FIG. 9 include but are not limited to:
1) Optionally uses one UV-C LED and relatively sleek and slender in size and shape, like a stick of lipstick.
2) Key chain style can include a clip.
3) Can be used for human skin in areas as described above.
4) Can include a disposable or rechargeable battery.
5) Can be made to be water resistant and/or waterproof.
6) Can include a child safety switch for on/off.
7) Can include a casing that includes silver oxide or copper to be naturally antimicrobial.
8) Cn be used on pets.
9) Can be used for gloves and other surfaces. This is especially useful for sanitizing surfaces in public like a restroom or other area.
10) The LED can be enclosed by quartz glass.
11) Allows for more directional focusing like hard to reach and "out of line of sight areas".
12) can include fluorescent color emitting options.

Figure 22:
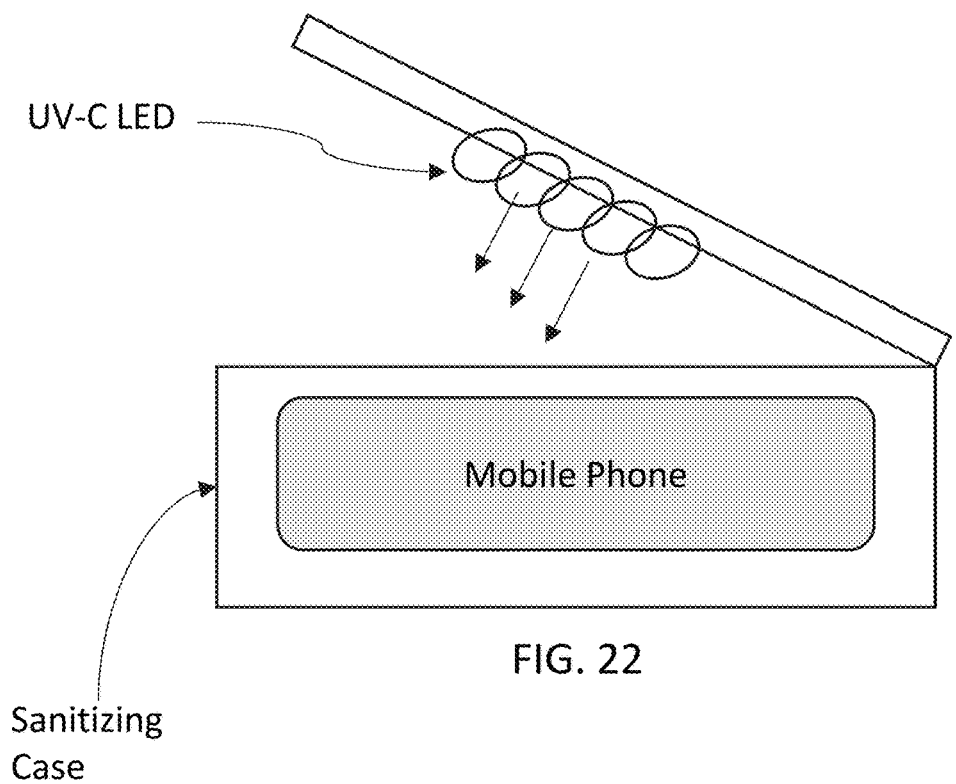
FIG. 22 is a schematic of a UV-C case or mobile phone coffin or carrying sanitizing case.

Referring to FIG. 22, the present disclosure further provides for a Mobile phone UV-C Disinfectant Coffin (carrying case or sanitizing case) that a mobile phone can be placed in to be sanitized when not in use or during charging, that offers the following benefits:
1) Solid state UVC technology as above.
2) Waterproof or water resistant
3) Used for mobile phones in carrying case.
4) Can be made to be rechargeable with low voltage cellphone cord as used for individual phone.
5) Only activates when case closed so there is no extra exposure.
6) Set timer for each time that the case is closed and has and on and off option.
7) Indicator light to know device is in use.
8) Silver Oxide or Copper casing for bacterial static external surface or being naturally antimicrobial.
9) Can use stronger UV-C wavelengths since no exposure to human tissues results since the case only activates when it is closed.

The present disclosure further provides for a One Last Time Orthopedic Sterilization device that is portable and able to further reduce or prevent unwanted and unnecessary exposure and/or infections during medical procedures and implant procedures like prosthetic orthopedic procedures. In this example, higher energy portable device can be used that further sterilizes prosthetic orthopedic equipment one last time before finally inserted into humans.

Figure 23:
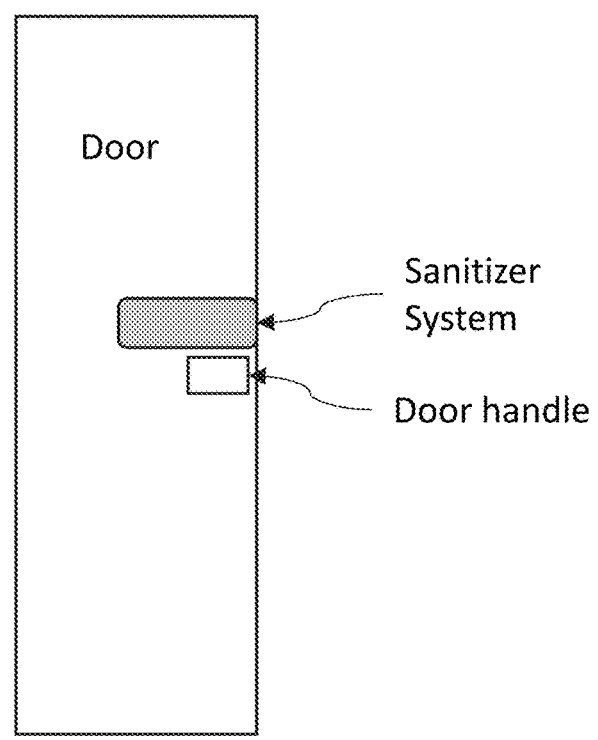
FIG. 23 is a schematic for a UV-C door handle sanitizing system.

Referring to FIG. 23, the present disclosure further provides for a Door Push Button Disinfectant Device that creates a constant or temporary UV-C light emission, which can be directed to a door handle and turned on between uses for a predetermined period of time. For example, a housing around or over a door handle can be introduced that includes UV-C LEDs and when turned on expose a surface of the door handle to the UV-C light. The LED's should be positioned in proximity to the door handle sufficient to sterilize when activated for a preset period of time, perhaps 5 seconds to 1 minute. The system can be configured with sensors to activate following any use, so each time someone touches the door handle to enter or leave a room. A safety cover can be provided to prevent undesired light exposure upward to prevent exposure to the eyes and the like.

Figure 24:
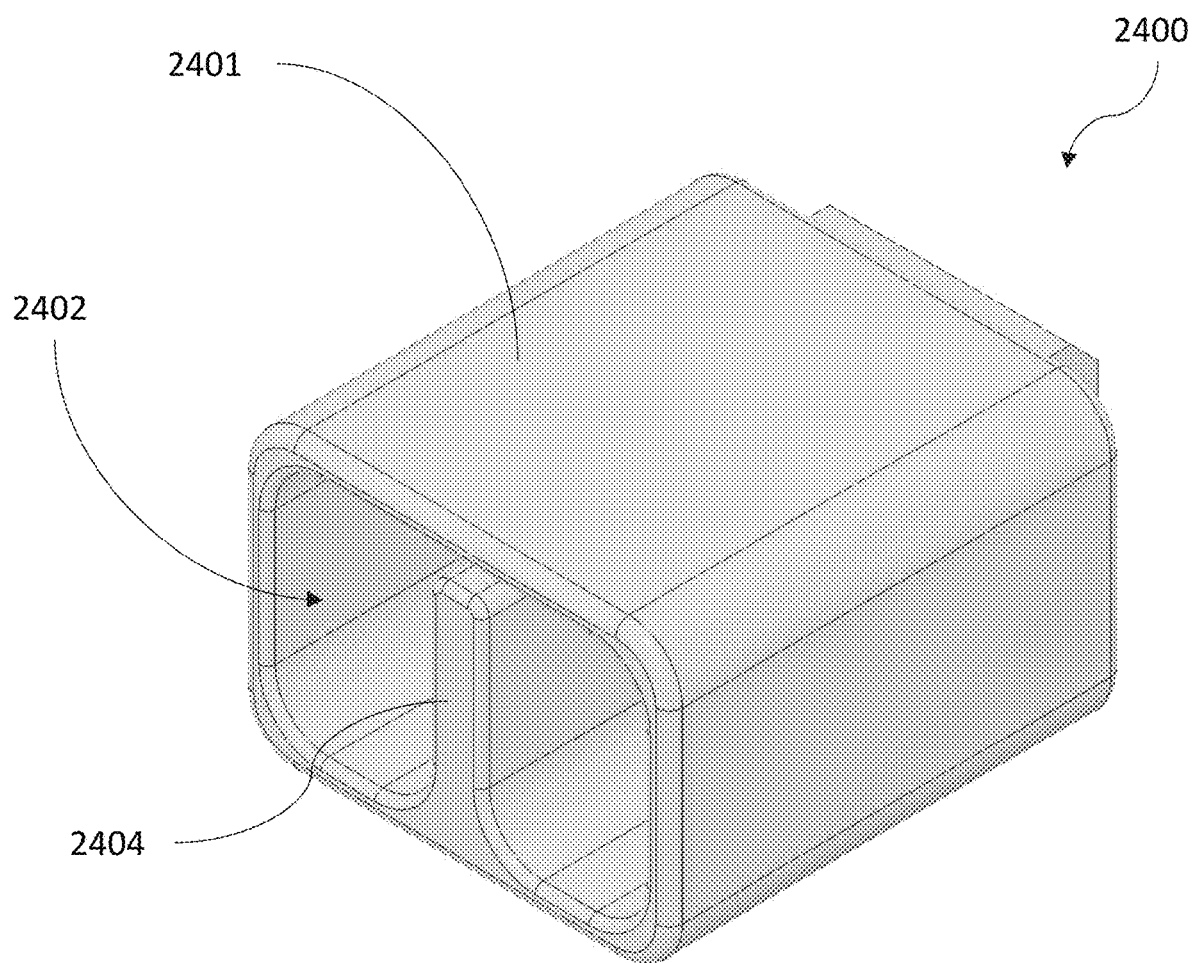
FIG. 24 is a schematic of a UV-C sanitizing enclosure according to the present disclosure.
Figure 25:
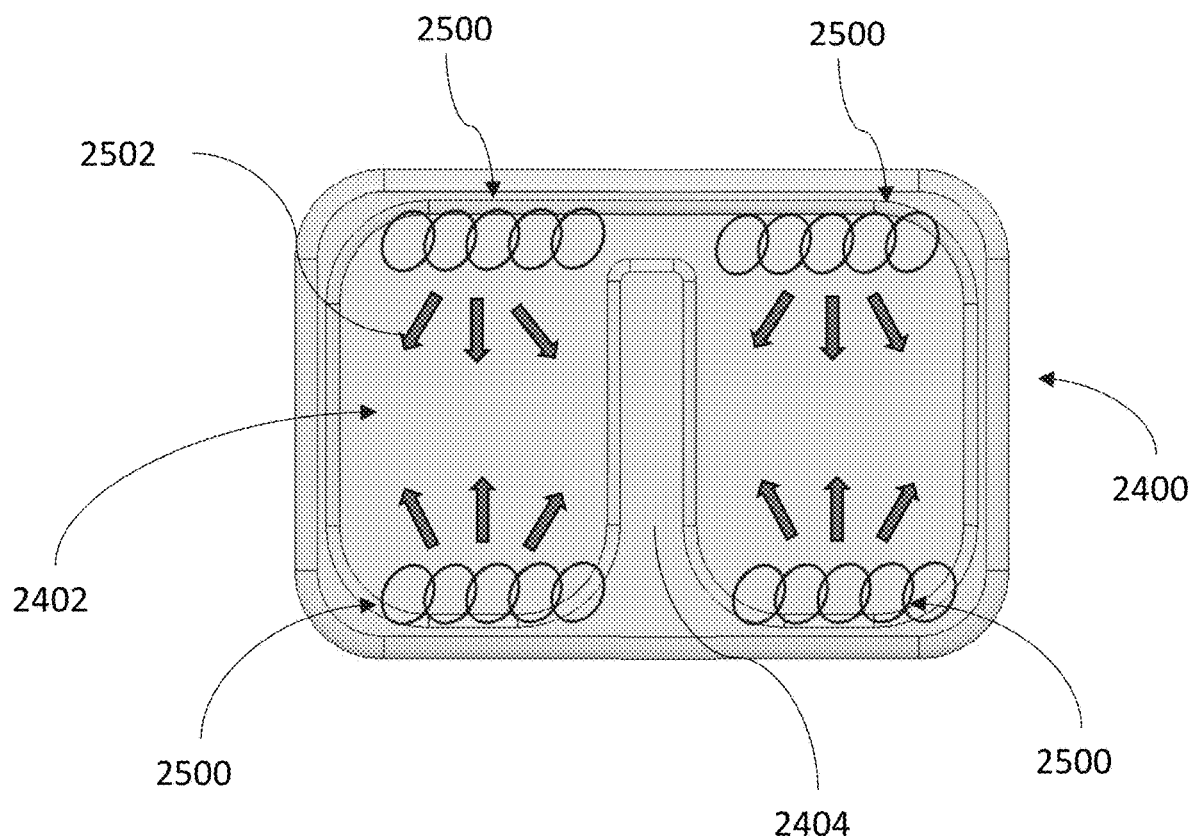
FIG. 25 illustrates a front view of the UV-C sanitizing enclosure of FIG. 24 demonstrating UV-C light emission schematically.

Referring to FIGS. 24 and 25, the present disclosure provides for a device 2400 which includes a UV-C light source 2500 of an emissions wavelength primarily between 205 nm and 210 nm. The device 2400 forms a main body or housing 2401 defining an opening 2402. In this example, the housing 2401 defines opening 2402 to receive one or more items intended to be sanitized, for example hands or gloves. A partition 2404 can be positioned within housing 2401 to form separate chambers for two hands or two gloves to be sanitized separately. The partition 2404 may extend fully or partially from the top or bottom surface of the interior of housing 2401 and may extend to abut the opposing surface or extend a portion of the height of housing 2401. Housing 2401 can be configured to reduce or prevent waste emissions from escaping the device and reduces or prevents unintended UV-C exposure to the user or bystanders.

The light source 2500 is arranged on the upper and lower surface of the enclosure. Positioning the light source 2500 on the upper and lower surface of the enclosure 2402 allows the light to be directed in close proximity to the surface of a hand or glove. Further, directing UV-C light from the bottom and top surfaces of the enclosure allows for sanitation of both sides of a hand or glove simultaneously.

The light source 2500 is capable of radiating light 2502 into a minimum of 240 degrees from its cylindrical or tile encapsulant. A user's hands or gloves may be placed within the enclosure 2402 of the device 2400. The radiated light 2502 may then be both manipulated and/or positioned to create a field by which one or more hand surfaces can be treated.

In an example, the device 2400 can control dosing based on hand size and time. The device 2400 may be configured to keep track of users by compiling report data such as number of uses and identification of users by biometric or other means. The device 2400 is capable of filtering output of the UV light such that wavelengths above a selected range are filtered out. For example, the device 2400 may filter output above 222 nm or 230 nm.

The present disclosure provides for a system which includes a UV-C light source 2500 of an emissions wavelength primarily between 205 and 210 nm directed to a surface of a hand or glove in close proximity. The light source 2500 of the system is capable of radiating light into a minimum of 240 degrees from its cylindrical or tile encapsulant. The radiated light is then both manipulated and positioned to create a field by which one or more hand surfaces can be treated. The system includes one or more sensors and one or more microprocessors in communication with the sensor.

In an example, the system can provide for user identification through a form of wireless communication either automatically or through a confirmation process. Examples for user identification and/or authentication include wireless or automated communication protocols and modules such as BLUETOOTH, facial recognition, biometric ID, and/or near field communications. The identification data may then be used to determine dosing in view of established kill rates of pathogens of interest. Additionally, the system analyzes the biometric, pathogen, and dosing data to determine a daily exposure threshold. The daily exposure thresholds are tracked such that daily exposure to any individual will not exceed local regulatory limits.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A UV-C sanitizing apparatus comprising:
   (a) a main body defining an opening configured for receiving an item to be exposed to UV-C light emission;
   (b) a plurality of UV-C light emitting diodes (LEDs) configured to emit UV-C light to form a field for treatment, the plurality of LEDS positioned on lower and upper internal surfaces of the main body;
   (c) a circuit board coupled to the plurality of LEDS and a power source operable to deliver power to the plurality of LEDS;
   wherein the plurality of LEDs are configured to emit light at a wavelength between 205 and 210 nm, and
   wherein the plurality of LEDs are configured to radiate light at a minimum of 240 degrees from a cylindrical or tile encapsulant.

2. The UV-C sanitizing apparatus according to claim 1, wherein the UV-C light is configured to kill, destroy, or reduce growth of microorganisms and germs without damaging human tissue.

3. The UV-C sanitizing apparatus according to claim 1, further comprising an on/off button positioned along an outside surface of the main body and coupled to the power source, wherein the button is configured for causing the plurality of LEDs to activate and deactivate.

4. The UV-C sanitizing apparatus of claim 1, wherein the power source is a battery selected from the group consisting of a disposable battery and a rechargeable battery.

5. The UV-C sanitizing apparatus of claim 1, wherein the UV-C light is configured to disinfect a surface of human hands or gloves.

6. The UV-C sanitizing apparatus of claim 1, wherein the UV-C light emitted is sufficient to disinfect a surface of ocular tissue.

7. The UV-C sanitizing apparatus of claim 1, further comprising one or more visible colored or fluorescent lights configured to activate when the apparatus turns on as an indication that the apparatus is emitting UV-C light.

8. The UV-C sanitizing apparatus of claim 1, wherein the main body includes a partition configured to form separate chambers and each chamber includes a plurality of LEDs positioned on the lower and upper surfaces of the main body.

9. The UV-C sanitizing apparatus of claim 8, wherein the partition extends fully or partially from the lower or upper surface of the main body configured to reduce or prevent waste emissions from escaping during use.

10. The UV-C sanitizing apparatus of claim 8, wherein the plurality of LEDs on the lower and upper surfaces of the main body are configured to sanitize from top and bottom sides of an item inserted through the opening simultaneously.

11. The UV-C sanitizing apparatus of claim 1, wherein the radiated light is configured to be manipulated to create a field by which one or more items can be treated.

12. The UV-C sanitizing apparatus of claim 1, further comprising a sensor and a controller having a microprocessor configured to adjust dosing based on item size and time of exposure.

13. The UV-C sanitizing apparatus of claim 12, further comprising a tracking module configured for tracking of users by compiling report data including number of uses and identification of users by biometric identification.

14. A UV-C sanitizing apparatus comprising:
   (a) a main body defining an opening configured for receiving an item to be exposed to UV-C light emission;

(b) a plurality of UV-C light emitting diodes (LEDs) configured to emit UV-C light to form a field for treatment, the plurality of LEDS positioned on lower and upper internal surfaces of the main body;

(c) a circuit board coupled to the plurality of LEDS and a power source operable to deliver power to the plurality of LEDS;

wherein the plurality of LEDs are configured to emit light at a wavelength between 205 and 210 nm, and further comprising a sensor and a controller having a microprocessor configured to adjust dosing based on item size and time of exposure.

15. The UV-C sanitizing apparatus of claim 14, further comprising a tracking module configured for tracking of users by compiling report data including number of uses and identification of users by biometric identification.

16. The UV-C sanitizing apparatus of claim 1, further comprising a filtering module configured for filtering output of the UV-C light at wavelengths above 222 nm.

17. The UV-C sanitizing apparatus of claim 1, further comprising a filtering module configured for filtering output of the UV-C light at wavelengths above 230 nm.

18. The UV-C sanitizing apparatus of claim 1, further comprising a user identification system having a wireless communication module configured for automatic authentication and confirmation through a confirmation process.

19. The UV-C sanitizing apparatus of claim 18, wherein the user identification and authentication includes wireless communication protocols and modules selected from the group consisting of facial recognition, biometric identification, near field communications, and combinations thereof.

20. The UV-C sanitizing apparatus of claim 19, wherein the identification and authentication of a user determines dosing of time and exposure intensity of UV-C light and wherein the dosing determination is configured to analyze biometric, pathogen, and dosing data to determine a daily exposure threshold such that daily exposure will not exceed regulatory limits.

* * * * *